(12) United States Patent
Sasaki et al.

(10) Patent No.: US 7,897,805 B2
(45) Date of Patent: Mar. 1, 2011

(54) POLYISOCYANATE PRODUCTION METHOD AND POLYISOCYANATE PRODUCTION SYSTEM

(75) Inventors: Masaaki Sasaki, Kamisu (JP); Takao Naito, Kamisu (JP); Fumiaki Hirata, Sodegaura (JP); Masato Saruwatari, Omuta (JP); Hirofumi Takahashi, Kamisu (JP); Kouji Maeba, Kamisu (JP); Tsugio Imaizumi, Kamisu (JP); Takuya Saeki, Omuta (JP); Takashi Yamaguchi, Omuta (JP); Kouichirou Terada, Omuta (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 1102 days.

(21) Appl. No.: 11/597,757
(22) PCT Filed: Mar. 8, 2006
(86) PCT No.: PCT/JP2006/304447

§ 371 (c)(1),
(2), (4) Date: Nov. 28, 2006

(87) PCT Pub. No.: WO2006/095761

PCT Pub. Date: Sep. 14, 2006

(65) Prior Publication Data

US 2008/0154066 A1 Jun. 26, 2008

(30) Foreign Application Priority Data

Mar. 10, 2005 (JP) .............................. 2005-068263
Mar. 10, 2005 (JP) .............................. 2005-068264

(51) Int. Cl.
*C07C 263/10* (2006.01)
(52) U.S. Cl. .................................................... 560/347
(58) Field of Classification Search ........................ None
See application file for complete search history.

(56) References Cited

U.S. PATENT DOCUMENTS 2,683,730 A * 7/1954 Seeger et al. ................. 560/359

4,774,070 A 9/1988 Itoh et al.

(Continued)

FOREIGN PATENT DOCUMENTS

JP 62-275001 A 11/1987

(Continued)

OTHER PUBLICATIONS

Notification Concerning Transmittal of International Preliminary Report on Patentability (Form PCT/IB/326), International Preliminary Report on Patentability (Form PCT/IB/373), Written Opinion of the International Search Authority (Form PCT/ISA/237) mailed in corresponding International Patent Application No. PCT/JP2006/304447, Sep. 20, 2007, The International Bureau of WIPO, Geneva, CH.

(Continued)

*Primary Examiner* — Daniel M Sullivan
*Assistant Examiner* — Yevegeny Valenrod
(74) *Attorney, Agent, or Firm* — Buchanan Ingersoll & Rooney PC

(57) ABSTRACT

A polyisocyanate production method that can allow effective use of hydrogen chloride produced secondarily in a polyisocyanate production process, while allowing reduction of environmental burdens, and a polyisocyanate production system for performing the polyisocyanate production method. After chlorine is allowed to react with carbon monoxide to produce carbonyl chloride in a carbonyl chloride producing reactor, the carbonyl chloride produced in the carbonyl chloride producing reactor is allowed to react with polyamine in an isocyanate producing reactor to produce polyisocyanate. Then, after hydrochloric gas produced secondarily in the isocyanate producing reactor is purified in a hydrogen chloride purifying column, the purified hydrochloric gas is oxidized in a hydrogen chloride oxidizing reactor to produce chlorine. Thereafter, the chlorine thus produced is supplied to the carbonyl chloride producing reactor from a chlorine resupply line, so that it is allowed to react with carbon monoxide to produce carbonyl chloride.

13 Claims, 4 Drawing Sheets

U.S. PATENT DOCUMENTS

| | | | |
|---|---|---|---|
| 5,849,947 | A | 12/1998 | Biskup et al. |
| 6,010,612 | A * | 1/2000 | Freire et al. .................. 205/551 |
| 6,472,564 | B1 | 10/2002 | Biskup et al. |
| 6,977,066 | B1 | 12/2005 | Iwanaga et al. |
| 7,588,739 | B2 | 9/2009 | Sugiyama et al. |
| 2003/0176626 | A1 | 9/2003 | Hagen et al. |
| 2004/0024244 | A1 | 2/2004 | Walsdorff et al. |
| 2006/0099138 | A1 | 5/2006 | Walsdorff et al. |

FOREIGN PATENT DOCUMENTS

| | | |
|---|---|---|
| JP | 9-52873 A | 2/1997 |
| JP | 2000-272906 A | 10/2000 |
| JP | 2001-516333 A | 9/2001 |
| JP | 2003-313155 A | 11/2003 |
| JP | 2004-035489 A | 2/2004 |
| JP | 2004-035492 A | 2/2004 |
| JP | 2004-217455 A | 8/2004 |
| WO | WO 97/24320 A1 | 7/1997 |
| WO | WO 2004/014845 A1 | 2/2004 |
| WO | WO 2004/037718 A2 | 5/2004 |
| WO | WO 2005/005037 A1 | 1/2005 |

OTHER PUBLICATIONS

Notification of Transmittal of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2006/304447, Aug. 21, 2008, The International Bureau of WIPO, Geneva, CH.

Office Action issued on Dec. 21, 2010, in corresponding Japanese Patent Application No. 2005-068264.

* cited by examiner

POLYISOCYANATE PRODUCTION METHOD AND POLYISOCYANATE PRODUCTION SYSTEM

TECHNICAL FIELD

The present invention relates to a polyisocyanate production method for producing polyisocyanate used as a raw material of polyurethane, and to a polyisocyanate production system for performing the polyisocyanate production method.

BACKGROUND ART

Polyisocyanate used as a raw material of polyurethane is industrially produced by allowing carbonyl chloride to react with polyamine for isocyanate reaction.

In this isocyanate reaction, corresponding polyisocyanate is produced from polyamine and a large quantity of hydrochloric gas is produced secondarily.

The hydrochloric gas produced secondarily is used for oxychlorination in production of vinyl chloride, for example.

Further, a production method for producing chlorine industrially by oxidizing the hydrochloric gas produced secondarily has been proposed (cf. Patent Document 1 and Patent Document 2, for example).

When hydrochloric gas is oxidized, water is also produced secondarily together with chlorine. The mixture of chlorine and water thus produced is dehydrated using a sulfuric acid to dry the chlorine, as is known (cf. Patent Document 3, for example).

Patent Document 1: Japanese Unexamined Patent Publication No. 62-275001,

Patent Document 2: Japanese Unexamined Patent Publication No. 2000-272906, and

Patent Document 3: Japanese Unexamined Patent Publication No. 2004-217455.

DISCLOSURE OF THE INVENTION

Problem to be Solved by the Invention

However, when production equipment of vinyl chloride is not located adjacent to production equipment of polyisocyanate, the hydrochloric gas produced secondarily in the isocyanate reaction cannot be utilized for oxychlorination in the production of the vinyl chloride.

When there is a user of chlorine in the same complex or production facility, the chlorine produced by oxidizing the hydrochloric gas produced secondarily can be used or sold for other application. It, however, requires an adjustment of an amount of polyisocyanate produced and an adjustment of an amount of chlorine produced in order to make a balance against other products, and also requires facilities, such as unused hydrogen chloride discharging equipment, costly high-pressure equipment for chlorine storage, and low-temperature equipment containing coolant. When there is no user of chlorine in the same complex or production facility, delivery equipment is also required in addition to the costly chlorine storage equipment. Under the circumstances, a production method for allowing use and consumption of the chlorine in the same complex or in the same location of production facilities is being desired.

When the hydrochloric gas produced secondarily is oxidized, chlorine and water are produced secondarily. When the mixture of chlorine and water thus produced is dehydrated using sulfuric acid, dried chlorine is obtained. On the other hand, since the sulfuric acid used in the drying absorbs water, a concentration of the sulfuric acid decreases.

It is desirable for improvement in dehydration efficiency that the concentration of sulfuric acid used for the dehydration is as high as not less than 97 weight %, for example. However, when the sulfuric acid is tried to be condensed to such a high concentration for the recycle use, a condensation process is additionally required, then causing cost rise. On the other hand, when the sulfuric acid used in the drying is disposed without being recycled, the sulfuric acid consumption increases, then still causing inevitable cost rise.

It is an object of the present invention to provide a polyisocyanate production method that can allow effective use of the hydrogen chloride produced secondarily in the polyisocyanate production process and can also allow reduction of environmental burdens, and to provide a polyisocyanate production system for performing the polyisocyanate production method.

It is another object of the present invention to provide a polyisocyanate production method that can make effective use of sulfuric acid used in the dehydration process to reduce production costs of polyisocyanate, and to provide a polyisocyanate production system for performing the polyisocyanate production method.

Means for Solving the Problem

To accomplish the objects described above, the present invention provides a polyisocyanate production method comprising a carbonyl chloride production process of producing carbonyl chloride by allowing chlorine to react with carbon monoxide, a polyisocyanate production process of producing polyisocyanate by allowing the carbonyl chloride produced in the carbonyl chloride production process to react with polyamine, and a chlorine production process of producing chlorine by oxidizing hydrogen chloride produced secondarily in the polyisocyanate production process, wherein the carbonyl chloride is produced by allowing the chlorine produced in the chlorine production process to react with carbon monoxide in the carbonyl chloride production process.

It is preferable that the polyisocyanate production method of the present invention further comprises a hydrochloric acid production process of producing the hydrochloric acid by allowing at least a part of the hydrogen chloride produced secondarily in the polyisocyanate production process and/or unoxidized hydrogen chloride in the chlorine production process to be absorbed or mixed in water.

In the polyisocyanate production method of the present invention, it is preferable that in the carbonyl chloride production process, corresponding to an amount of hydrogen chloride required for the hydrochloric acid produced in the hydrochloric acid production process, chlorine is additionally supplied together with the chlorine produced in the chlorine production process.

In the polyisocyanate production method of the present invention, it is preferable that at least a part of the carbonyl chloride produced in the carbonyl chloride production process is put in a liquefied state and/or a solution state before the reaction with polyamine.

The present invention provides a polyisocyanate production method comprising a polyamine production process of producing polymethylene polyphenylene polyamine by allowing aniline to react with formaldehyde, using acid catalyst containing hydrochloric acid, a carbonyl chloride production process of producing carbonyl chloride by allowing chlorine to react with carbon monoxide, a polyisocyanate production process of producing polymethylene polyphenylene polyisocyanate by allowing the carbonyl chloride produced in the carbonyl chloride production process to react with polymethylene polyphenylene polyamine produced in the polyamine production process, a chlorine production process of producing chlorine by oxidizing hydrogen chloride produced secondarily in the polyisocyanate production process, and a hydrochloric acid production process of producing the hydrochloric acid by allowing at least a part of the hydrogen chloride produced secondarily in the polyisocyanate production process and/or unoxidized hydrogen chloride in the chlorine production process to be absorbed or mixed in water, wherein the chlorine produced in the chlorine production process is allowed to react with carbon monoxide in the carbonyl chloride production process to produce carbonyl chloride, and the hydrochloric acid produced in the hydrochloric acid production process is used as the acid catalyst in the polyamine production process.

The present invention provides a polyisocyanate production method comprising a carbonyl chloride production process of producing carbonyl chloride by allowing chlorine to react with carbon monoxide, a polyisocyanate production process of producing tolylene diisocyanate by allowing the carbonyl chloride produced in the carbonyl chloride production process to react with tolylene diamine, a chlorine production process of producing chlorine by oxidizing hydrogen chloride produced secondarily in the polyisocyanate production process, a hydrochloric acid production process of producing the hydrochloric acid by allowing at least a part of the hydrogen chloride produced secondarily in the polyisocyanate production process and/or unoxidized hydrogen chloride in the chlorine production process to be absorbed or mixed in water, wherein the chlorine produced in the chlorine production process is allowed to react with carbon monoxide in the carbonyl chloride production process to produce carbonyl chloride.

Further, the present invention provides a polyisocyanate production system comprising a carbonyl chloride production unit for producing carbonyl chloride by allowing chlorine to react with carbon monoxide, a polyisocyanate production unit for producing polyisocyanate by allowing the carbonyl chloride produced in the carbonyl chloride production unit to react with polyamine, a chlorine production unit for producing chlorine by oxidizing hydrogen chloride produced secondarily in the polyisocyanate production unit, and a chlorine resupply unit for resupplying the chlorine produced in the chlorine production unit to the carbonyl chloride production unit, to allow the chlorine to react with carbon monoxide in the carbonyl chloride production unit to produce carbonyl chloride.

The present invention provides a polyisocyanate production system comprising a polyamine production unit for producing polymethylene polyphenylene polyamine by allowing aniline to react with formaldehyde, using acid catalyst containing hydrochloric acid, a carbonyl chloride production unit for producing carbonyl chloride by allowing chlorine to react with carbon monoxide, a polyisocyanate production unit for producing polymethylene polyphenylene polyisocyanate by allowing the carbonyl chloride produced in the carbonyl chloride production unit to react with the polymethylene polyphenylene polyamine produced in the polyamine production unit, a chlorine production unit for producing chlorine by oxidizing hydrogen chloride produced secondarily in the polyisocyanate production unit, a hydrochloric acid production unit for producing the hydrochloric acid by allowing at least a part of hydrogen chloride produced secondarily in the polyisocyanate production unit and/or unoxidized hydrogen chloride in the chlorine production unit to be absorbed or mixed in water, a chlorine resupply unit for resupplying the chlorine produced in the chlorine production unit to the carbonyl chloride production unit, to allow the chlorine to react with carbon monoxide in the carbonyl chloride production unit to produce carbonyl chloride, and a hydrochloric acid resupply unit for resupplying the hydrochloric acid produced in the hydrochloric acid production unit to the polyamine production unit, to use the hydrochloric acid as the acid catalyst in the polyamine production unit.

The present invention provides a polyisocyanate production system comprising a carbonyl chloride production unit for producing carbonyl chloride by allowing chlorine to react with carbon monoxide, a polyisocyanate production unit for producing tolylene diisocyanate by allowing the carbonyl chloride produced in the carbonyl chloride production unit to react with tolylene diamine, a chlorine production unit for producing chlorine by oxidizing hydrogen chloride produced secondarily in the polyisocyanate production unit, a hydrochloric acid production unit for producing the hydrochloric acid by allowing at least a part of the hydrogen chloride produced secondarily in the polyisocyanate production unit and/or unoxidized hydrogen chloride in the chlorine production unit to be absorbed or mixed in water, and a chlorine resupply unit for resupplying the chlorine produced in the chlorine production unit to the carbonyl chloride production unit, to allow the chlorine to react with carbon monoxide in the carbonyl chloride production unit to produce carbonyl chloride.

Further, the present invention provides a polyisocyanate production method comprising a carbonyl chloride production process of producing carbonyl chloride by allowing chlorine to react with carbon monoxide, a polyisocyanate production process of producing polyisocyanate by allowing the carbonyl chloride produced in the carbonyl chloride production process to react with polyamine, and a chlorine production process of producing chlorine to be used in the carbonyl chloride production process by oxidizing hydrogen chloride produced secondarily in the polyisocyanate production process, wherein a start-up operation is first performed by starting production of carbonyl chloride in the chlorine production process, starting production of polyisocyanate in the polyisocyanate production process, and starting production of chlorine in the chlorine production process, then a load-up operation, in which any one of the processes, i.e., the process of increasing an amount of carbonyl chloride produced in the carbonyl chloride production process, the process of increasing an amount of polyisocyanate produced in the polyisocyanate production process, and the process of increasing an amount of chlorine produced in the chlorine production process, is selectively performed, and then the two other processes are performed is repeatedly performed until an amount of polyisocyanate produced reaches a predetermined amount.

According to the polyisocyanate production method of the present invention, since the chlorine to be used in the carbonyl chloride production process is produced in the chlorine production process by oxidizing the hydrogen chloride produced secondarily in the polyisocyanate production process, the chlorine produced can be allowed to react with carbon monoxide in the carbonyl chloride production process thereby to produce carbonyl chloride. This means that the chlorine can be produced from the hydrogen chloride produced secondarily, and then the chlorine can be reused as the raw material of the carbonyl chloride. This can allow the recycle use of chlorine without being drained to the outside of a system, which can allow efficient use of the hydrogen chloride produced secondarily, while allowing reduction of environmental burdens.

Further, in this method, Cl atoms circulate in the system and a predetermined amount of polyisocyanate is constantly produced. This requires that the start-up operation at the starting of the operation and the load-up operation from the starting of the operation until the predetermined amount of polyisocyanate being constantly produced are performed effectively.

In this method, the start-up operation is first performed by starting production of carbonyl chloride in the chlorine production process, starting production of polyisocyanate in the polyisocyanate production process, and starting production of chlorine in the chlorine production process, then the load-up operation, in which any one of the processes, i.e., the process of increasing an amount of carbonyl chloride produced in the carbonyl chloride production process, the process of increasing an amount of polyisocyanate produced in the polyisocyanate production process, and the process of increasing an amount of chlorine produced in the chlorine production process, is selectively performed, and then the two other processes are performed, is repeatedly performed until an amount of polyisocyanate produced reaches a predetermined amount. This can realized an effective operation by increasing the amount of polyisocyanate produced in each process overall and stepwise until the amount of polyisocyanate produced reaches a predetermined amount.

According to the polyisocyanate production method of the present invention, this can allow effective use of the hydrogen chloride produced secondarily in the polyisocyanate production process, while allowing reduction of environmental burdens. Further, this can also realize the effective operation by increasing the amount of polyisocyanate produced in each process overall and stepwise until the amount of polyisocyanate produced reaches a predetermined amount.

In the polyisocyanate production method of the present invention, it is preferable that in the start-up operation, after the production of the carbonyl chloride starts in the carbonyl chloride production process, the production of polyisocyanate starts in the polyisocyanate production process and then the production of chlorine starts in the chlorine production process.

In the polyisocyanate production method of the present invention, it is preferable that in the load-up operation, after an amount of carbonyl chloride produced is increased in the carbonyl chloride production process, an amount of polyisocyanate produced is increased in the polyisocyanate production process and then an amount of chlorine produced is increased in the chlorine production process.

In the polyisocyanate production method of the present invention, it is preferable that in the chlorine production process, the hydrogen chloride is oxidized in a fluid bed reactor, and that in the start-up operation, a warming-up operation of the fluid bed reactor is performed before the production of chlorine starts in the chlorine production process.

In the polyisocyanate production method of the present invention, it is preferable that in the chlorine production process, the hydrogen chloride is oxidized in a fixed bed reactor, and that in the start-up operation, a warming-up operation of the fixed bed reactor is performed before the production of chlorine starts in the chlorine production process.

The present invention provides a polyisocyanate production method comprising a carbonyl chloride production process of producing carbonyl chloride by allowing chlorine to react with carbon monoxide, a polyisocyanate production process of producing polyisocyanate by allowing the carbonyl chloride produced in the carbonyl chloride production process to react with polyamine, and a chlorine production process of producing chlorine to be used in the carbonyl chloride production process by oxidizing hydrogen chloride produced secondarily in the polyisocyanate production process, wherein a start-up operation, in which after chlorine of raw material previously prepared and carbon monoxide are allowed to react with each other in the carbonyl chloride production process to produce carbonyl chloride, the carbonyl chloride produced is allowed to react with polyamine in the polyisocyanate production process to produce polyisocyanate and then the hydrogen chloride produced secondarily is oxidized in the chlorine production process to produce chlorine to be used in the carbonyl chloride production process, is first performed, and then a load-up operation, in which after the chlorine of raw material and the chlorine produced in the chlorine production process are allowed to react with carbon monoxide in the carbonyl chloride production process to produce carbonyl chloride, the carbonyl chloride produced is allowed to react with polyamine in the polyisocyanate production process to produce polyisocyanate and then the hydrogen chloride produced secondarily is oxidized in the chlorine production process to produce chlorine to be used in the carbonyl chloride production process, is repeatedly performed until an amount of polyisocyanate produced reaches a predetermined amount.

According to the polyisocyanate production method of the present invention, since the chlorine to be used in the carbonyl chloride production process is produced in the chlorine production process by oxidizing the hydrogen chloride produced secondarily in the polyisocyanate production process, the chlorine produced can be allowed to react with carbon monoxide in the carbonyl chloride production process thereby to produce carbonyl chloride. This means that the chlorine can be produced from the hydrogen chloride produced secondarily, and then the chlorine can be reused as the raw material of the carbonyl chloride. This can allow the recycle use of chlorine without being drained to the outside of the system, which can allow efficient use of the hydrogen chloride produced secondarily, while allowing reduction of environmental burdens.

In this method, Cl atoms circulate in the system and a predetermined amount of polyisocyanate produced is constantly produced. This requires that the start-up operation at the starting of the operation and the load-up operation from the starting of the operation until the predetermined amount of polyisocyanate being constantly produced are performed effectively.

In this method, the start-up operation, in which after chlorine of raw material previously prepared and carbon monoxide are allowed to react with each other in the carbonyl chloride production process to produce carbonyl chloride, the carbonyl chloride produced is allowed to react with polyamine in the polyisocyanate production process to produce polyisocyanate and then the hydrogen chloride produced secondarily is oxidized in the chlorine production process to produce chlorine to be used in the carbonyl chloride production process, is first performed. Then, a load-up operation, in which after the chlorine of raw material and the chlorine produced in the chlorine production process are allowed to react with carbon monoxide in the carbonyl chloride production process to produce carbonyl chloride, the carbonyl chloride produced is allowed to react with polyamine in the polyisocyanate production process to produce polyisocyanate and then the hydrogen chloride produced secondarily is oxidized in the chlorine production process to produce chlorine to be used in the carbonyl chloride production process, is repeatedly performed until an amount of polyisocyanate produced reaches a predetermined amount. This can realize an effective operation by increasing the amount of polyisocyanate produced in each process overall and stepwise until the amount of polyisocyanate produced reaches a predetermined amount.

In the polyisocyanate production method of the present invention, it is preferable that a fixed amount of chlorine of raw material is used in the carbonyl chloride production process in the start-up operation as well as in the carbonyl chloride production process in the load-up operation.

The present invention provides a polyisocyanate production method comprising a polyamine production process of producing polymethylene polyphenylene polyamine by allowing aniline to react with formaldehyde, using acid catalyst containing hydrochloric acid, a carbonyl chloride production process of producing carbonyl chloride by allowing chlorine to react with carbon monoxide, a polyisocyanate production process of producing polymethylene polyphenylene polyisocyanate by allowing the carbonyl chloride produced in the carbonyl chloride production process to react with the polymethylene polyphenylene polyamine produced in the polyamine production process, a chlorine production process of producing chlorine to be used in the carbonyl chloride production process by oxidizing hydrogen chloride produced secondarily in the polyisocyanate production process, and a hydrochloric acid production process of producing hydrochloric acid to be used as the acid catalyst in the polyamine production process by allowing at least a part of the hydrogen chloride produced secondarily in the polyisocyanate production process and/or unoxidized hydrogen chloride in the chlorine production process to be absorbed or mixed in water, wherein a start-up operation is first performed by starting production of polymethylene polyphenylene polyamine in the polyamine production process, starting production of carbonyl chloride in the carbonyl chloride production process, starting production of polymethylene polyphenylene polyisocyanate in the polyisocyanate production process, starting production of chlorine in the chlorine production process, and starting production of hydrochloric acid in the hydrochloric acid production process, and then a load-up operation, in which any one of the five processes, i.e., the process of increasing an amount of polymethylene polyphenylene polyamine produced in the polyamine production process, the process of increasing an amount of carbonyl chloride produced in the carbonyl chloride production process, the process of increasing an amount of polyisocyanate produced in the polyisocyanate production process, the process of increasing an amount of chlorine produced in the chlorine production process, and the process of increasing an amount of hydrochloric acid produced in the hydrochloric acid production process, is selectively performed, and then the four other processes are performed is repeatedly performed until an amount of polymethylene polyphenylene polyisocyanate produced reaches a predetermined amount.

According to the polyisocyanate production method of the present invention, the hydrochloric acid used for producing polymethylene polyphenylene polyamine can be produced from the hydrogen chloride produced secondarily in the production of polymethylene polyphenylene polyisocyanate.

The present invention provides a polyisocyanate production method comprising a nitration process of nitrating an aromatic raw material, using a sulfuric acid and a nitric acid, to introduce a nitro group in an aromatic ring of the aromatic raw material, a polyamine production process of producing polyamine by reducing the nitro group introduced in the aromatic ring of the aromatic raw material in the nitration process to an amino group, a carbonyl chloride production process of producing carbonyl chloride by allowing chlorine to react with carbon monoxide, a polyisocyanate production process of producing polyisocyanate by allowing the carbonyl chloride produced in the carbonyl chloride production process to react with the polyamine produced in the polyamine production process, a hydrogen chloride oxidation process of oxidizing hydrogen chloride produced secondarily in the polyisocyanate production process to produce a mixture of chlorine and water, and a dehydration process of dehydrating the mixture produced in the hydrogen chloride oxidation process by putting the mixture into contact with a sulfuric acid thereby to produce chlorine, wherein the sulfuric acid used in the dehydration process is reused in the nitration process.

According to this method, the sulfuric acid used in the dehydration process can be reused to nitrate the aromatic raw material in the nitration process. This can allow effective use of sulfuric acid and can reduce production costs of polyisocyanate.

In the polyisocyanate production method of the present invention, since in the dehydration process, after the mixture and the sulfuric acid are supplied to a dehydration column continuously so that they are continuously contacted with each other in the dehydration column, the sulfuric acid absorbing the water is drained continuously, it is preferable that an amount of sulfuric acid supplied per unit time in the dehydration process is adjusted to correspond to an amount of sulfuric acid lost per unit time in the nitration process.

When an amount of sulfuric acid supplied per unit time in the dehydration process is adjusted to correspond to an amount of sulfuric acid lost per unit time in the nitration process, there is no need to add the sulfuric acid in the nitration process, thus allowing further effective use of the sulfuric acid.

In the polyisocyanate production method of the present invention, it is preferable that in the dehydration process, a concentration of sulfuric acid supplied to the dehydration column is not less than 97 weight %.

When the concentration of sulfuric acid supplied to the dehydration column is not less than 97 weight %, the dehydration efficiency can be improved remarkably.

Further, in the polyisocyanate production method of the present invention, it is preferable that the chlorine produced in the dehydration process is allowed to react with carbon monoxide in the carbonyl chloride production process to produce carbonyl chloride.

When the chlorine produced in the dehydration process is allowed to react with carbon monoxide in the carbonyl chloride production process to produce carbonyl chloride, the chlorine can be used without being drained to the outside of the system, which can allow efficient use of the hydrogen chloride produced secondarily, while allowing reduction of environmental burdens.

The present invention provides a polyisocyanate production system comprising a nitration reactor for nitrating an aromatic raw material, using a sulfuric acid and a nitric acid, to introduce a nitro group in an aromatic ring of the aromatic raw material, a polyamine producing reactor for producing polyamine by reducing the nitro group introduced in the aromatic ring of the aromatic raw material in the nitration reactor to an amino group, a carbonyl chloride producing reactor for producing carbonyl chloride by allowing chlorine to react with carbon monoxide, a polyisocyanate producing reactor for producing polyisocyanate by allowing the carbonyl chloride produced in the carbonyl chloride producing reactor to react with the polyamine produced in the polyamine producing reactor, a hydrogen chloride oxidizing reactor for oxidizing hydrogen chloride produced secondarily in the polyisocyanate producing reactor to produce a mixture of chlorine and water, a dehydration column for dehydrating the mixture produced in the hydrogen chloride oxidizing reactor by putting the mixture into contact with a sulfuric acid thereby to produce chlorine, and a sulfuric acid supply line for supplying the sulfuric acid from the dehydration column to the nitration reactor so that the sulfuric acid used in the dehydration column can be reused in the nitration process.

According to this system, the sulfuric acid used in the dehydration column is reused to nitrate an aromatic raw material in the nitration reactor by supplying the sulfuric acid from the dehydration column to the nitration reactor via the sulfuric acid supply line. This can allow efficient use of the sulfuric acid, which can realize reduction of production costs of polyisocyanate.

It is preferable that the polyisocyanate production system of the present invention further comprises a chlorine supply line for supplying the chlorine produced in the dehydration column from the dehydration column to the carbonyl chloride producing reactor so that the chlorine is allowed to react with carbon monoxide in the carbonyl chloride producing reactor to produce carbonyl chloride.

When the chlorine produced in the dehydration column is supplied from the dehydration column to the carbonyl chloride producing reactor via the chlorine supply line, the chlorine can be allowed to react with carbon monoxide in the carbonyl chloride producing reactor to produce carbonyl chloride. This can allow the recycle use of chlorine without being drained to the outside of the system, which can allow efficient use of the hydrogen chloride produced secondarily, while allowing reduction of environmental burdens.

Effect of the Invention

According to the polyisocyanate production method of the present invention, after chlorine is produced in the chlorine production process by oxidizing the hydrogen chloride produced secondarily in the polyisocyanate production process, the chlorine produced is allowed to react with carbon monoxide in the carbonyl chloride production process thereby to produce carbonyl chloride. In short, the chlorine is produced from the hydrogen chloride produced secondarily and the chlorine thus produced is reused as the raw material of the carbonyl chloride. This can allow the recycle use of chlorine without being drained to the outside of the system, which can allow efficient use of the hydrogen chloride produced secondarily, while allowing reduction of environmental burdens.

According to the polyisocyanate production system of the present invention, after chlorine is produced in the chlorine production unit by oxidizing the hydrogen chloride produced secondarily in the polyisocyanate production unit, the chlorine produced is supplied to the carbonyl chloride production unit via the chlorine resupply unit so that the chlorine can be allowed to react with carbon monoxide in the carbonyl chloride production process thereby to produce carbonyl chloride. In short, chlorine is produced from the hydrogen chloride produced secondarily and the chlorine thus produced is reused as the raw material of the carbonyl chloride. This can allow the recycle use of chlorine without being drained to the outside of the system, which can allow efficient use of the hydrogen chloride produced secondarily, while allowing reduction of environmental burdens.

EXPLANATION OF NUMERALS

Figure 1:
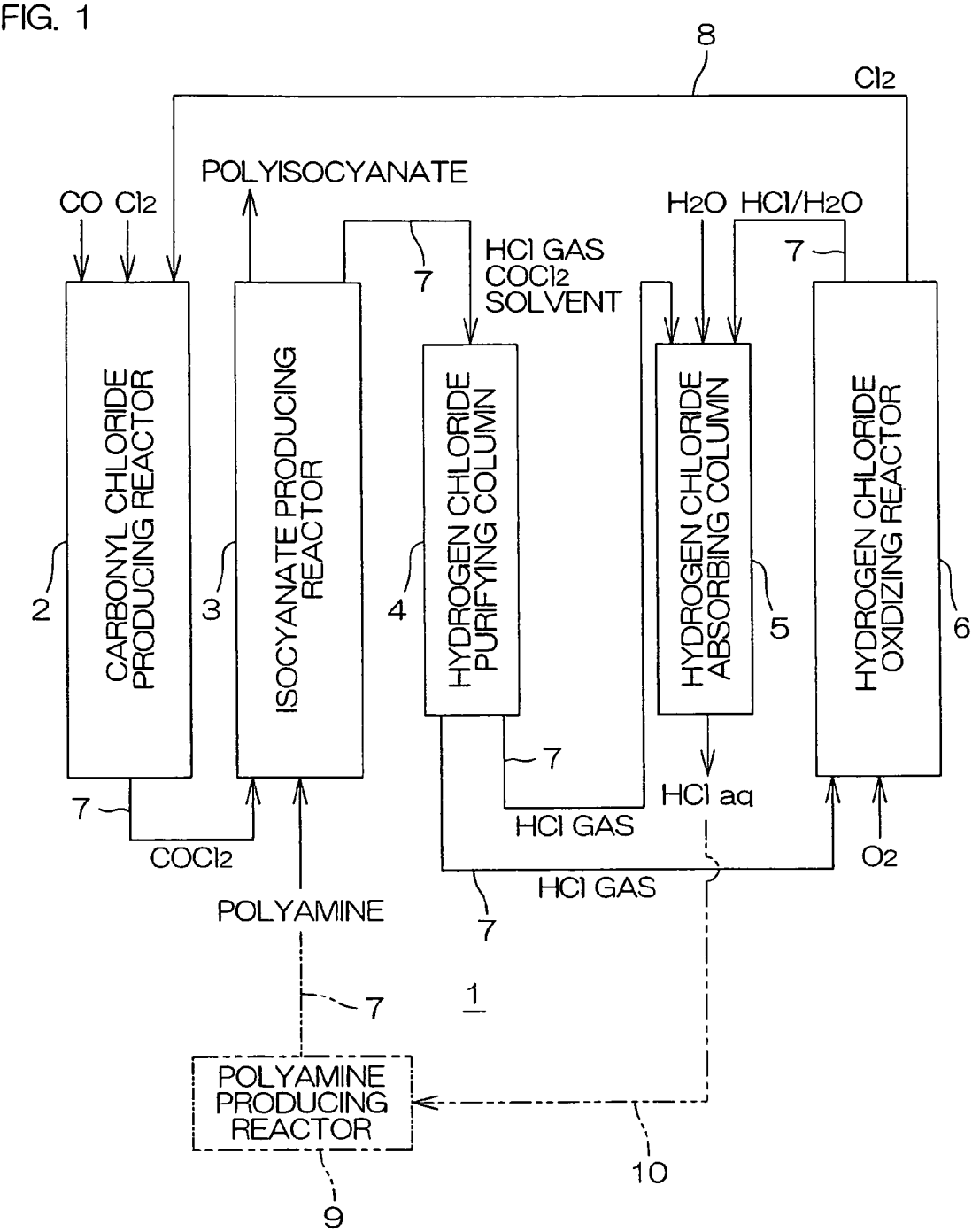
FIG. 1 is a schematic block diagram showing an embodiment of a polyisocyanate production system of the present invention.

1: Polyisocyanate production system
2: Carbonyl chloride producing reactor
3: Isocyanate producing reactor
5: Hydrogen chloride absorbing column
6: Hydrogen chloride oxidizing reactor
8: Chlorine reuse (resupply) line
9: Polyamine producing reactor
10: Hydrochloric acid reuse (resupply) line
21: Polyisocyanate production system
22: Nitration reactor
23: Polyamine producing reactor
24: Carbonyl chloride producing reactor
25: Polyisocyanate producing reactor
28: Hydrogen chloride oxidizing reactor
29: Dehydration column
31: Sulfuric acid supply line
32: Chlorine supply line

EMBODIMENTS OF THE INVENTION

FIG. 1 is a schematic block diagram showing an embodiment of a polyisocyanate production system of the present invention. In the following, an embodiment of the polyisocyanate production method of the present invention is described with reference to FIG. 1.

As shown in FIG. 1, a polyisocyanate production system 1 comprises a carbonyl chloride producing reactor 2 for serving as carbonyl chloride production unit, an isocyanate producing reactor 3 serving as polyisocyanate production unit, a hydrogen chloride purifying column 4, a hydrogen chloride absorbing column 5 serving as hydrochloric acid production unit, a hydrogen chloride oxidizing reactor 6 serving as chlorine production unit, connection lines (piping) 7 for connection therebetween, and a chlorine resupply line 8 serving as chlorine resupply unit.

The carbonyl chloride producing reactor 2 is not limited to any particular one, as long as it is a reactor for reacting chlorine ($Cl_2$) with carbon monoxide (CO) to produce carbonyl chloride ($COCl_2$). For example, the carbonyl chloride producing reactor 2 includes a fixed bed reactor in which activate carbon catalyst is packed. Further, the carbonyl chloride producing reactor 2 is connected to an isocyanate producing reactor 3 via a connection line 7.

Chlorine gas and carbon monoxide gas, which are raw materials of carbonyl chloride, are supplied to the carbonyl chloride producing reactor 2 in such a proportion that carbon monoxide is supplied more than chlorine by 1-10 mol. When chlorine is oversupplied, there is a possibility that an aromatic ring and a hydrogen chloride group of polyisocyanate may be chlorinated in the isocyanate producing reactor 3 by the oversupplied chlorine.

An amount of chlorine gas supplied and an amount of carbon monoxide supplied are properly determined on the basis of an amount of polyisocyanate produced and an amount of hydrogen chloride gas produced secondarily.

In the carbonyl chloride producing reactor 2, chlorine and carbon monoxide undergo carbonyl chloridation reaction to produce carbonyl chloride (carbonyl chloride production process). In this carbonyl chloridation reaction, the carbonyl chloride producing reactor 2 is set at 0-500° C. and 0-5 MPa gauge, for example.

The carbonyl chloride obtained may be put in a liquefied state by being properly cooled to be liquefied, or may be put in a solution state by being absorbed in an adequate solvent, in the carbonyl chloride producing reactor 2 or in separate equipment, not shown.

When at least a part of carbonyl chloride is put in the liquefied state and/or solution state, a concentration of carbon monoxide contained in the carbonyl chloride can be reduced. This can reduce a concentration of carbon monoxide gas contained in the hydrogen chloride gas produced secondarily in isocyanate reaction mentioned later, thus improving a ratio of conversion of hydrogen chloride to chlorine in an oxidation reaction of hydrogen chloride mentioned later. This can improve purity of the chlorine resupplied from the chlorine reuse line 8 to the carbonyl chloride producing reactor 2, as mentioned later.

This means that when a concentration of carbon monoxide contained in the carbonyl chloride obtained in the carbonyl chloride production process is reduced, a concentration of carbon monoxide circulated in the polyisocyanate production system can be reduced.

Accordingly, a concentration of carbon monoxide contained in carbonyl chloride in the liquefied state and/or the solution state is preferably 1 weight % or less, or more preferably 0.2 weight % or less.

When carbonyl chloride is in the liquefied state, a concentration of carbon monoxide within a system for polyisocyanate production extending from the polyisocyanate production process to the chlorine production process can be reduced remarkably. As a result of this, improvement of basic unit and improvement of operation performance can be realized in the chlorine production process.

Then, the carbonyl chloride thus obtained is supplied to the isocyanate producing reactor 3 via the connection line 7.

The isocyanate producing reactor 3 is not limited to any particular one, as long as it is a reactor for reacting carbonyl chloride with polyamine to produce polyisocyanate. The isocyanate producing reactor 3 includes a reactor equipped with a stirring vane and a reaction column having a perforated plate. Preferably, the isocyanate producing reactor 3 is configured as a multistage tank. The isocyanate producing reactor 3 is connected to the hydrogen chloride purifying column 4 through the connection line 7.

The carbonyl chloride as a raw material of polyisocyanate produced in the carbonyl chloride producing reactor 2 is supplied from the carbonyl chloride producing reactor 2 to the isocyanate producing reactor 3 via the connection line 7 together with polyamine as a raw material of polyisocyanate.

In the isocyanate reaction in the isocyanate producing reactor 3, a solvent or gas inactive to polyisocyanate may also be used properly.

The carbonyl chloride is supplied from the carbonyl chloride producing reactor 2 in a gaseous state as it is or in the above-mentioned liquefied or solution state in such a proportion that carbonyl chloride is supplied more than polyamine by 1-60 mol, or preferably by 1-10 mol.

Polyamine used is polyamine corresponding to polyisocyanate used in the production of polyurethane. No particular limitation is imposed on polyamine. For example, polyamine is properly selected from aromatic diamines, such as polymethylene polyphenylene polyamine (MDA) corresponding to polymethylene polyphenylene polyisocyanate (MDI) and tolylene diamine (TDA) corresponding to tolylene diisocyanate (TDI), aralkyl diamines, such as xylylenediamine (XDA) corresponding to xylylenediisocyanate (XDI) and tetramethylxylylene diamine (TMXDA) corresponding to tetramethylxylylene diisocyanate (TMXDI), alicyclic diamines, such as bis(aminomethyl)norbornane (NBDA) corresponding to bis(isocyanatomethyl)norbornane (NBDI), 3-aminomethyl-3,5,5-trimethylcyclohexyl amine (IPDA) corresponding to 3-isocyanatomethyl-3,5,5-trimethylcyclohexyl isocyanate (IPDI), 4,4'-methylenebis(cyclohexylamine) ($H_{12}$MDA) corresponding to 4,4'-methylenebis(cyclohexylisocyanate) ($H_{12}$MDI), and bis(aminomethyl) cyclohexane ($H_6$XDA) corresponding to bis(isocyanatomethyl)cyclohexane ($H_6$XDI), aliphatic diamines, such as hexamethylene diamine (HDA) corresponding to hexamethylene diisocyanate (HDI), and polymethylene polyphenyl polyamine corresponding to polymethylene polyphenyl polyisocyanate (crude MDI, polymeric MDI).

The polyisocyanate production system 1 is suitable for producing aromatic diisocyanate and polymethylene polyphenyl polyisocyanate from aromatic diamine and polymethylene polyphenyl polyamine.

Though polyamine may be supplied directly, it is preferable that polyamine is previously dissolved in a solvent to produce e.g. a 5-30 weight % or preferably 10-25 weight % solution before being supplied.

The solvent used is not limited to any particular one. The solvents that may be used include, for example, aromatic hydrocarbons, such as toluene and xylene, halogenated hydrocarbons, such as chlorotoluene, chlorobenzene, and dichlorobenzene, esters, such as butyl acetate and amyl acetate, and ketones, such as methylisobutyl ketone and methylethyl ketone. Preferably, chlorobenzene and dichlorobenzene can be used.

In the isocyanate producing reactor 3, the carbonyl chloride and the polyamine undergo isocyanate reaction to produce polyisocyanate, while also hydrochloric gas (HCl gas) is produced secondarily (polyisocyanate production process). In the isocyanate reaction, the above-mentioned solvent is added in the isocyanate producing reactor 3 separately or together with polyamine and the isocyanate producing reactor 3 is set at 0-500° C. and 0-5 MPa-gauge, for example.

The obtained polyisocyanate undergoes aftertreatments, such as degasification, desolvating, and tar cut, and is then purified, before it is provided as the raw material of polyurethane.

The hydrochloric gas produced secondarily is supplied to the hydrogen chloride purifying column 4 via the connection line 7, together with the entrained solvent and carbonyl chloride.

The hydrogen chloride purifying column 4 is not limited to any particular one, as long as it can purify the hydrochloric gas produced secondarily by separating the entrained solvent and carbonyl chloride therefrom. For example, the hydrogen chloride purifying column 4 includes a tray column and a packed column which are equipped with a condenser. The hydrogen chloride purifying column 4 is connected to the hydrogen chloride absorbing column 5 and the hydrogen chloride oxidizing reactor 6 through the connection line 7.

In the hydrogen chloride purifying column 4, the carbonyl chloride is condensed by the condenser or absorbed by the solvent, whereby the carbonyl chloride is separated from the hydrochloric gas. Further, a slight amount of solvent in the hydrogen chloride is separated from the hydrochloric gas by being absorbed in activated carbon and the like.

In the hydrogen chloride purifying column 4, a concentration of an organic material in the hydrochloric gas is reduced to be 1 weight % or less, preferably 0.5 weight % or more preferably 0.1 weight % or less, and a concentration of carbon monoxide in the hydrochloric gas is reduced to be 10V/V % or less, or preferably 3V/V % or less.

By reducing impurities in the hydrochloric gas to such a level, disadvantageous effects on the catalyst, such as decreased activity or partial deactivation of the catalyst, can be reduced or prevented in the hydrogen chloride oxidation reaction mentioned later. This can achieve an improved basic unit and an equalized temperature distribution of the hydrogen chloride oxidizing reactor 6 and thus stabilization of the hydrogen chloride oxidizing reactor 6. Further, this can improve a ratio of hydrogen chloride to chlorine.

Then, a large proportion of the hydrochloric gas purified is supplied to the hydrogen chloride oxidizing reactor 6 and a part of the hydrochloric gas purified is supplied to the hydrogen chloride absorbing column 5. A proportion between the hydrochloric gas supplied to the hydrogen chloride oxidizing reactor 6 and the hydrochloric gas supplied to the hydrogen chloride absorbing column 5 is properly determined on the basis of a desired concentration of the hydrochloric acid in the hydrogen chloride absorbing column 5, as mentioned later.

The hydrogen chloride oxidizing reactor 6 is not limited to any particular one, as long as it is a reactor for oxidizing the hydrochloric gas to produce chlorine ($Cl_2$). For example, the hydrogen chloride oxidizing reactor 6 includes a fluid bed reactor using chromium oxide as the catalyst and a fixed bed reactor using ruthenium oxide as the catalyst.

The hydrogen chloride oxidizing reactor 6 is connected to the carbonyl chloride producing reactor 2 via a chlorine resupply line 8 and is connected to the hydrogen chloride absorbing column 5 via the connection line 7.

When the hydrogen chloride oxidizing reactor 6 comprises the fluid bed reactor, at least 0.25 mol of oxygen per mol of hydrogen chloride contained in the hydrochloric gas is supplied to the fluid bed reactor 6 for the reaction in the presence of chromium oxide at 0.1-5 MPa-gauge and 300-500° C., with reference to Japanese Unexamined Patent Publication No. 62-275001, for example. An amount of hydrochloric gas supplied is in the range of e.g. 0.2-1.8 $Nm^3$/h·kg-catalyst.

When the hydrogen chloride oxidizing reactor 6 comprises the fixed bed reactor, at least 0.25 mol of oxygen per mol of hydrogen chloride contained in the hydrochloric gas is supplied to the fixed bed reactor 6 for the reaction in the presence of ruthenium-containing catalyst at 0.1-5 MPa and 200-500° C., with reference to Japanese Unexamined Patent Publication No. 2000-272906, for example.

Then, in the hydrogen chloride oxidizing reactor 6, the hydrochloric gas is oxidized by oxygen ($O_2$), so that chlorine is produced and water ($H_2O$) is produced secondarily (chlorine production process). In the hydrogen chloride oxidation reaction, a conversion ratio of hydrogen chloride to chlorine is e.g. 60% or more, or preferably 70-95%.

The chlorine obtained is purified on an as-needed basis by a known process including absorption, dehydration, and separation, though not shown in particular.

Then, in the polyisocyanate production system 1, the chlorine obtained in the hydrogen chloride oxidizing reactor 6 is supplied to the carbonyl chloride producing reactor 2 via the chlorine resupply line 8 and is reused as a raw material for producing the carbonyl chloride in the carbonyl chloride producing reactor 2.

As just described, in the polyisocyanate production method using this polyisocyanate production system 1, after the hydrogen chloride produced secondarily in the isocyanate producing reactor 3 is oxidized to produce chlorine in the hydrogen chloride oxidizing reactor 6, the chlorine thus produced is supplied to the carbonyl chloride producing reactor 2 and is reused as the raw material of the carbonyl chloride. Thus, this method can allow the recycle use of chlorine without being drained to the outside of the system of the polyisocyanate production system 1, which can allow efficient use of the hydrogen chloride produced secondarily, while allowing reduction of environmental burdens.

Unoxidized (unreacted) hydrogen chloride gas and hydrochloric acid water in the hydrogen chloride oxidizing reactor 6 are supplied therefrom to the hydrogen chloride absorbing column 5 via the connection line 7. The hydrochloric acid water is produced by making the hydrochloric gas being absorbed in the water produced secondarily in the hydrogen chloride oxidizing reactor 6.

The hydrogen chloride absorbing column 5 is not limited to any particular one, as long as it can adjust a concentration of the hydrochloric acid water (aqueous solution of hydrogen chloride: HClaq) by making the hydrogen chloride gas absorbed in water or hydrochloric acid water. The hydrogen chloride absorbing column 5 includes a known absorbing column.

Water, the hydrochloric gas and hydrochloric acid water supplied from hydrogen chloride oxidizing reactor 6 via the connection line 7, and the hydrochloric gas supplied from the hydrogen chloride purifying column 4 via the connection line 7 are supplied to the hydrogen chloride absorbing column 5, in which the hydrochloric gas is absorbed in the water and the hydrochloric acid water thereby to produce hydrochloric acid (hydrochloric acid production process). The hydrochloric acid thus obtained is provided for industrial purpose as it is or after purified using activated carbon and the like.

Since the hydrochloric acid produced in the hydrogen chloride absorbing column 5 is provided in a desired concentration for industrial purpose without any need to change, a concentration of the hydrochloric acid (a concentration of hydrogen chloride contained in the hydrochloric acid) is adjusted to a desired value by regulating an amount of water supplied to the hydrogen chloride absorbing column 5 or by regulating an amount of hydrochloric gas supplied from the hydrogen chloride purifying column 4 via the connection line 7. Alternatively, a concentration of the hydrochloric acid may be adjusted in such a process that after the hydrochloric acid once absorbed is heated to produce hydrochloric gas again, the hydrochloric gas thus reproduced is absorbed in a predetermined amount of water.

The hydrogen chloride is converted to chlorine at a constant conversion ratio in the hydrogen chloride oxidizing reactor 6, so that the remaining hydrogen chloride after conversion to the chlorine is supplied from the hydrogen chloride oxidizing reactor 6 to the hydrogen chloride absorbing column 5 via the connection line 7 at a fixed ratio. For example, where the conversion ratio in the hydrogen chloride oxidizing reactor 6 is 80%, 80% hydrogen chloride is converted to chlorine, while on the other hand, the remaining 20% hydrogen chloride is supplied from in the hydrogen chloride oxidizing reactor 6 to the hydrogen chloride absorbing column 5 via the connection line 7.

Then, a concentration of the hydrochloric acid is adjusted to a desired value by regulating a volume of water supplied to the hydrogen chloride absorbing column 5 on the basis of the hydrochloric gas and the hydrochloric acid water supplied from the hydrogen chloride oxidizing reactor 6 and the hydrochloric gas supplied from the hydrogen chloride purifying column 4, or by regulating a quantity of the hydrochloric gas supplied from the hydrogen chloride purifying column 4 on the basis of the hydrochloric gas supplied from the hydrogen chloride oxidizing reactor 6. This can provide the result that a desired concentration of the hydrochloric acid can be prepared in the hydrogen chloride absorbing column 5 without any need to adjust the concentration in a subsequent process, which can allow the hydrochloric acid to be directly provided for the industrial purpose.

In this polyisocyanate production system 1, chlorine (added chlorine) separately prepared as a raw material is also supplied to the carbonyl chloride producing reactor 2, in addition to the chlorine (the recycled chlorine) supplied thereto from the hydrogen chloride oxidizing reactor 6 via the chlorine resupply line 8.

An amount of added chlorine supplied is set to correspond to a required amount of hydrogen chloride for producing the hydrochloric acid in the hydrogen chloride absorbing column 5 (that is a shortage of the recycled chlorine). The added chlorine may be purchased from outside, if required. Alternatively, the polyisocyanate production system may include added chlorine production equipment for producing chlorine by a process such as electrolyzation separate from the polyisocyanate production method so that the added chlorine may be supplied from such added chlorine production equipment.

When the added chlorine is supplied in correspondence with the required amount of added chlorine for producing the hydrochloric acid in the hydrogen chloride absorbing column 5, a mass balance in the polyisocyanate production system 1 can be stabilized, while the hydrochloric acid of a desired concentration can be provided from the hydrogen chloride absorbing column 5.

Then, when tolylene diisocyanate (TDI) in particular is produced by the polyisocyanate production system 1, carbonyl chloride is supplied from the carbonyl chloride producing reactor 2 to the isocyanate producing reactor 3 via the connection line 7 and tolylene diamine (TDA) is also supplied thereto as the polyamine.

In the isocyanate producing reactor 3, the TDI is produced by the reaction between the carbonyl chloride and the TDA.

When the TDI is produced by this polyisocyanate production system 1, there can be provided the result that the hydrogen chloride produced secondarily can be used effectively, while environmental burdens can be reduced, as mentioned above.

In the case where the polymethylene polyphenylene polyisocyanate (MDI) is produced in the polyisocyanate production system 1 cited above, the polyisocyanate production system 1 includes a polyamine producing reactor 9 serving as polyamine producing unit for producing polymethylene polyphenylene polyamine (MDA), as indicated by a dotted line.

The polyamine producing reactor 9 is not limited to any particular one, as long as it can allow aniline and formaldehyde to react with each other using the acid catalyst comprising the hydrochloric acid thereby to produce the MDA. The polyamine producing reactor 9 includes, for example, a reactor equipped with a stirring vane and a reactor having a perforated plate. Preferably, the polyamine producing reactor 9 is configured as a multistage tank. The polyamine producing reactor 9 is connected to the isocyanate producing reactor 3 via the connection line 7 and also is connected to the hydrogen chloride absorbing column 5 via a hydrochloric acid resupply line 10 serving as hydrochloric acid resupply unit.

The aniline and the formaldehyde, which are raw materials of polyamine, are supplied to the polyamine producing reactor 9. The hydrochloric acid is also supplied thereto as the acid catalyst. This hydrochloric acid is the hydrochloric acid produced in the hydrogen chloride absorbing column 5 and supplied therefrom to the reactor 9 via the hydrochloric acid resupply line 10. The hydrogen acid is supplied thereto separately, as required. In the reaction between the aniline and the formaldehyde, the inactive solvent and the inactive gas may be used properly.

A supply ratio between the aniline and the formaldehyde is properly selected by a desired multimeric complex ratio of the MDA. In the polyamine producing reactor 9, the formaldehyde may be supplied in a multistage manner to the aniline.

The amount of aniline supplied, the amount of formaldehyde supplied, and the amount of acid catalyst supplied are properly set on the basis of an amount of polyisocyanate produced and an amount of hydrochloric gas produced secondarily.

In the polyamine producing reactor 9, the aniline and the formaldehyde react with each other to produce the MDA (polyamine production process). Then, the MDA thus produced is supplied to the isocyanate producing reactor 3 via the connection line 7. In the isocyanate producing reactor 3, the MDI is produced by the isocyanate reaction between the carbonyl chloride and the MDA.

When the MDI is produced by this polyisocyanate production system 1, there can be provided the result that the hydrogen chloride produced secondarily can be used effectively, while environmental burdens can be reduced, as mentioned above.

When the MDI is produced by this polyisocyanate production system 1, the hydrochloric acid produced in the hydrogen chloride absorbing column 5 is supplied to the polyamine producing reactor 9 via the hydrochloric acid resupply line 10. Then, the hydrochloric acid is used as the acid catalyst in the reaction between the aniline and the formaldehyde in the polyamine producing reactor 9. This means that the hydrogen chloride produced secondarily in the isocyanate reaction of the MDI can fill the need for the hydrochloric acid used as the acid catalyst in the production of the MDA. This can achieve improvement in production efficiency and reduction in production cost.

In the polyisocyanate production system 1 mentioned above, since Cl atoms circulate in the system and a predetermined amount of polyisocyanate produced is constantly produced, as described above, it is required that a start-up operation at the start of operation and a load-up operation from the start of the operation until the start of steady operation are performed effectively.

Figure 2:
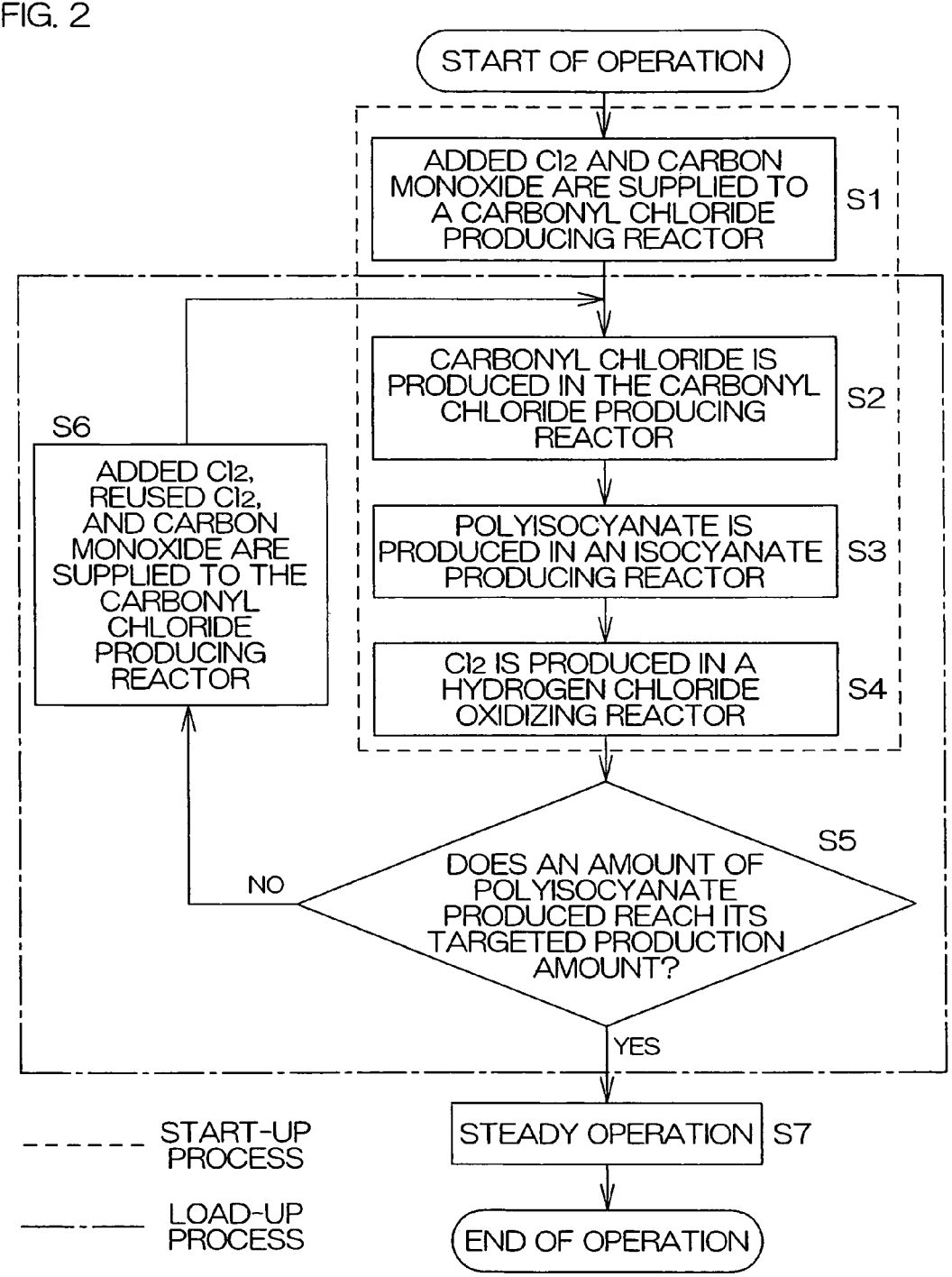
FIG. 2 is a flowchart showing an embodiment of the sequence of a start-up operation and a load-up operation of the polyisocyanate production system shown in FIG. 1.

FIG. 2 is a flowchart showing an embodiment of the sequence of the start-up operation and the load-up operation of the polyisocyanate production system shown in FIG. 1.

Next, description on the start-up operation and the load-up operation of this polyisocyanate production system 1 is given with reference to FIG. 2.

As shown in FIG. 2, the added chlorine only is used in the start-up operation (S1-S4) at the starting of the operation. To be more specific, the added chlorine and carbon monoxide are supplied to the carbonyl chloride producing reactor 2 (S1), first. The amount of added chlorine supplied is e.g. 10-50%, or preferably 10-30% where the amount of added chlorine supplied during the steady operation is 100%.

Then, in the carbonyl chloride producing reactor 2, carbonyl chloride is produced by the carbonyl chloridation reaction between the chlorine and the carbon monoxide (S2).

Then, the carbonyl chloride produced in the carbonyl chloride producing reactor 2 is allowed to react with polyamine in the isocyanate producing reactor 3, whereby polyisocyanate is produced and hydrochloric gas is produced secondarily (S3).

Thereafter, the hydrochloric gas produced secondarily is purified in the hydrogen chloride purifying column 4 and then oxidized in the hydrogen chloride oxidizing reactor 6 thereby to produce recycled chlorine (S4).

Then, in this polyisocyanate production system 1, the load-up operation (S2-S6) is repeatedly performed during the time from the start of operation until the start of steady operation. To be more specific, in addition to the added chlorine, the recycled chlorine produced in the hydrogen chloride oxidizing reactor 6 is supplied to the carbonyl chloride producing reactor 2, together with the carbon monoxide, first (S6).

The amount of chlorine supplied in this load-up operation comes to be a total of the added chlorine and the recycled chlorine. Hence, the amount of chlorine supplied in this load-up operation is more than the amount of chlorine supplied in the start-up operation. For example, when 25% of the added chlorine is supplied in the start-up operation and a conversion ratio of hydrogen chloride to chlorine is 80%, 20% of the recycled chlorine is produced in the start-up operation and that 20% of the recycled chlorine is added to 25% of the added chlorine in the load-up operation, i.e., 45% of the chlorine is originally supplied in the load-up operation.

Then, in the carbonyl chloride producing reactor 2, the carbonyl chloride is produced by the carbonyl chloridation reaction between the chlorine and the carbon monoxide (S2). The amount of carbonyl chloride thus produced increases with the amount of chlorine supplied.

Then, the carbonyl chloride produced in the carbonyl chloride producing reactor 2 is allowed to react with polyamine in the isocyanate producing reactor 3, whereby polyisocyanate is produced and hydrochloric gas is produced secondarily (S3). The amount of polyisocyanate thus produced and the amount of hydrochloric gas produced secondarily increase with increase in amount of carbonyl chloride produced.

Thereafter, the hydrochloric gas produced secondarily is purified in the hydrogen chloride purifying column 4 and then oxidized in the hydrogen chloride oxidizing reactor 6 thereby to produce the recycled chlorine (S4). The amount of recycled chlorine thus produced increases with an amount of hydrochloric gas produced secondarily. For example, when 45% of the chlorine is originally supplied in the load-up operation and a conversion ratio of hydrogen chloride to chlorine is 80%, 36% of the recycled chlorine is produced.

Then, the processes mentioned above (S6-S4) are repeatedly performed until the amount of polyisocyanate produced reaches its targeted production amount (i.e. the amount of polyisocyanate produced in the steady operation), (S5: NO). In these repeated processes, the amount of carbonyl chloride produced, the amount of polyisocyanate produced, the amount of hydrochloric gas produced secondarily, and the amount of recycled chlorine produced increase with increase in amount of chlorine supplied in each cycle. For example, when 36% of the recycled chlorine is produced, as mentioned above, 36% of the recycled chlorine is added to 25% of the added chlorine, so that an amount of chlorine supplied next amounts to 61%. With the increase in amount of chlorine supplied, the amount of carbonyl chloride produced, the amount of polyisocyanate produced, the amount of hydrochloric gas produced secondarily, and the amount of recycled chlorine produced secondarily increase.

When the amount of polyisocyanate produced increases gradually and reaches its targeted production amount (i.e. the amount of polyisocyanate produced in the steady operation), the load-up operation ends (S5:YES) and then the steady operation proceeds (S7).

In the steady operation, an amount of chlorine supplied to the carbonyl chloride producing reactor 2 (a total amount of added chlorine and recycled chlorine) is fixed corresponding to the amount of polyisocyanate produced in the steady operation.

No particular limitation is imposed on the way of fixing the amount of chlorine supplied. The amount of chlorine supplied may be fixed by the following method, for example. Namely, a certain amount of added chlorine is constantly supplied during the time from the start of operation until the start of steady operation, while on the other hand, an amount of hydrochloric gas produced secondarily in the isocyanate producing reactor 3 to be absorbed directly in water and hydrochloric acid water in the hydrogen chloride absorbing column 5 after purified by the hydrogen chloride purifying column 4 is adjusted (increased) in the steady operation. This can allow a certain amount of added chlorine to be supplied constantly, facilitating calculation of the mass balance and the control of the system.

The amount of chlorine supplied may be fixed by the following alternate method, for example. Namely, the amount of added chlorine may be decreased than that in the load-up operation so that the amount of chlorine supplied to the carbonyl chloride producing reactor 2 (a total amount of added chlorine and recycled chlorine) can be made constant in the steady operation.

When the start-up operation and the load-up operation are performed in the steps mentioned above, the effective operation can be realized by allowing the amount produced in each process to be increased overall and stepwise until the amount of polyisocyanate produced reaches an amount of polyisocyanate produced in the steady operation.

In the above description, the amount of carbonyl chloride produced is increased in the carbonyl chloride producing reactor 2 and then the amount of polyisocyanate produced is increased in the isocyanate producing reactor 3, then the amount of recycled chlorine produced is increased in the hydrogen chloride oxidizing reactor 6, the sequence of the process of the load-up operation can be selectively determined in the polyisocyanate production system 1.

The load-up operation may be performed in the following sequences, for example. After the amount of polyisocyanate produced is increased in the isocyanate producing reactor 3 by adjusting the amount of polyamine supplied in the isocyanate producing reactor 3, the amount of recycled chlorine is increased in the hydrogen chloride oxidizing reactor 6 and then the amount of carbonyl chloride produced is increased in the carbonyl chloride producing reactor 2.

Further, the load-up operation may alternatively be performed in the following sequences, for example. After the amount of hydrochloric gas produced secondarily in the isocyanate producing reactor 3 to be absorbed directly in water and hydrochloric acid water in the hydrogen chloride absorbing column 5 after purified in the hydrogen chloride purifying column 4 is adjusted (increased) to increase the amount of recycled chlorine produced in the hydrogen chloride oxidizing reactor 6, the amount of carbonyl chloride produced is increased in the carbonyl chloride producing reactor 2 and then the amount of polyisocyanate produced is increased in the isocyanate producing reactor 3.

It is preferable that in the start-up operation, the warming-up operation is performed before the recycled chlorine is produced in the hydrogen chloride oxidizing reactor 6.

In the case where the hydrogen chloride oxidizing reactor 6 comprises the fluid bed reactor, the fluid bed reactor is previously put in an circulation operation to be set at a predetermined temperature and pressure, using e.g. an inactive gas, such as nitrogen, or air, chlorine, or an inactive gas containing chlorine, or hydrogen chloride, before the hydrochloric gas is supplied to the hydrogen chloride oxidizing reactor 6.

When the fluid bed reactor is thus previously put in a circulation operation, the start-up operation can be performed further effectively.

Figure 3:
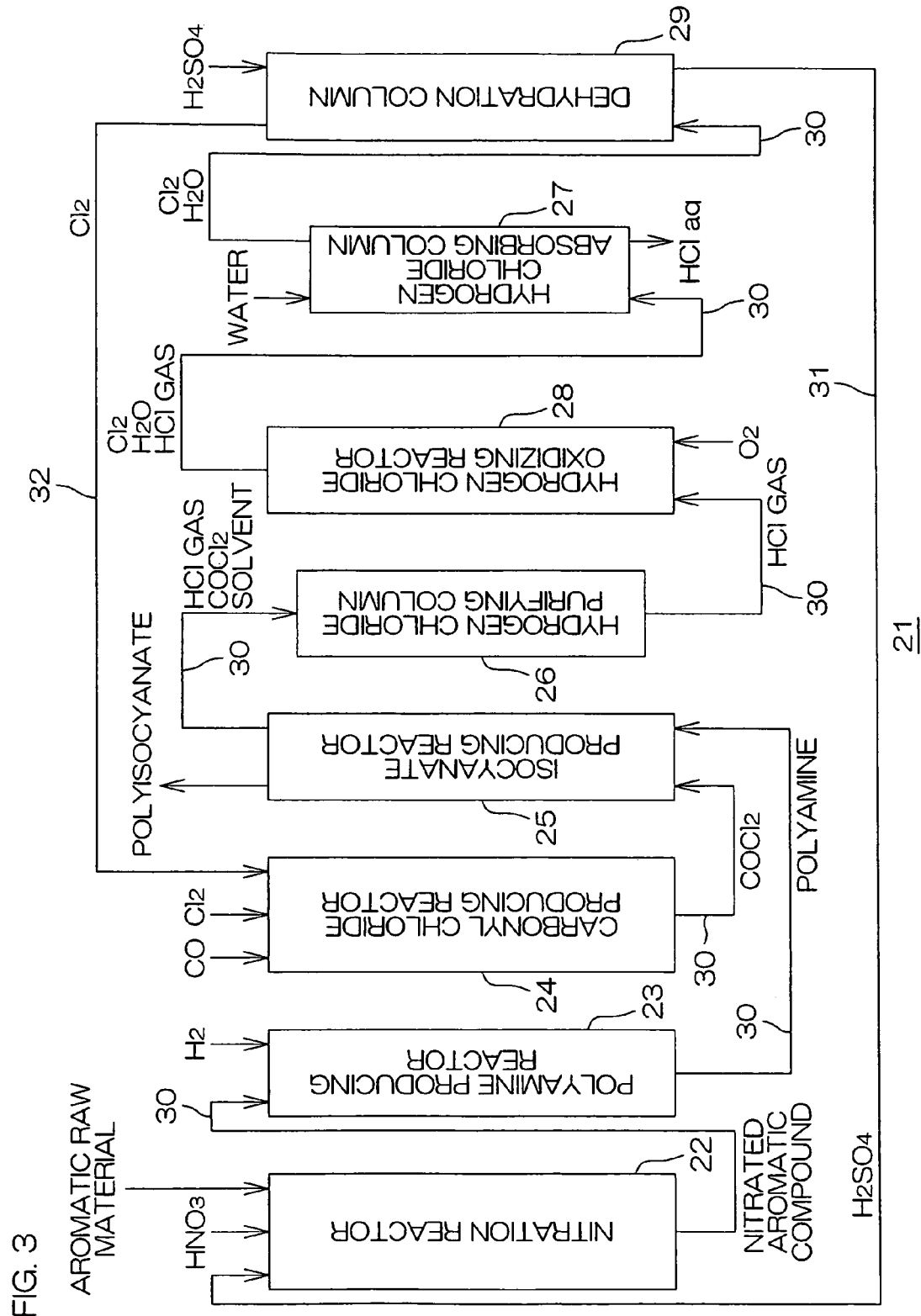
FIG. 3 is a schematic block diagram showing another embodiment of the polyisocyanate production system of the present invention.

FIG. 3 is a schematic block diagram showing another embodiment of the polyisocyanate production system of the present invention. In the following, another embodiment of the polyisocyanate production system of the present invention is described with reference to FIG. 3.

As shown in FIG. 3, a polyisocyanate production system 21 comprises a nitration reactor 22, a polyamine producing reactor 23, a carbonyl chloride producing reactor 24, a polyisocyanate producing reactor 25, a hydrogen chloride purifying column 26, a hydrogen chloride absorbing column 27, a hydrogen chloride oxidizing reactor 28, a dehydration column 29, a connection line (piping) 30 for connecting them, a sulfuric acid supply line 31, and a hydrochloric acid supply line 32.

The nitration reactor 22 is not limited to any particular one, as long as it is a reactor for performing nitration of aromatic raw material using sulfuric acid and nitric acid. The nitration reactor 22 includes, for example, a reactor equipped with a stirring vane and a reactor having a perforated plate. Preferably, the nitration reactor 22 is configured as a multistage tank. Further, the nitration reactor 22 is connected to the polyamine producing reactor 23 via the connection line 30.

The aromatic raw material and the nitric acid are continuously supplied to the nitration reactor 22 and the sulfuric acid used in circulation in the nitration process. Further, an amount of sulfuric acid corresponding to an amount of sulfuric acid lost per unit time in the nitration process is continuously supplied from the dehydration column 29 to the nitration reactor 22.

The aromatic raw material which includes benzenes and derivatives thereof is selected from e.g. benzene, toluene, etc. corresponding to polyisocyanate produced. Specifically, when polymethylene polyphenylene polyisocyanate (MDI) is produced, benzene is used and mononitrated in the nitration reactor 22. On the other hand, when tolylene diisocyanate (TDI) is produced, toluene is used and dinitrated in the nitration reactor 22.

For example, 50-100 weight % nitric acid (aqueous solution) is used as the nitric acid. In the mononitration, the nitric acid is continuously supplied in the proportion of e.g. 0.7-1.5 mol, or preferably 0.8-1.2 mol, per mol of aromatic raw material. On the other hand, in the dinitration, the nitric acid is continuously supplied in the proportion of e.g. 1.5-2.5 mol, or preferably 1.6-2.2 mol, per mol of aromatic raw material.

The sulfuric acid supplemented corresponding to the amount lost in the nitration process is, for example, 60-100 weight %, or preferably 70-98 weight %, sulfuric acid (aqueous solution). It is supplied continuously from the dehydration column 29 via the sulfuric acid supply line 31, as mentioned later.

In the nitration reactor 22, the aromatic raw material contacts with sulfuric acid and nitric acid (mixed acid) and is nitrated (more specifically, mononitrated when benzene is used, and dinitrated when toluene is used), so that one or two nitro groups is/are introduced in an aromatic ring of the aromatic raw material (in the nitration process). In this nitration process, the nitration reactor 22 is set at e.g. 0-200° C., or preferably 30-180° C.

As a result of this, a nitrated aromatic compound having one or two nitro groups introduced in the aromatic ring is produced in the nitration reactor 22. More concretely, when benzene is used as the aromatic raw material, nitrobenzene is produced as the nitrated aromatic compound. On the other hand, when toluene is used as the aromatic raw material, dinitrotoluene is produced as the nitrated aromatic compound.

In this process, a nitric acid contained in the mixed acid is consumed in the nitration reaction and also water is produced. The mixed acid used for the reaction is diluted with product water and introduced water from the aqueous nitric acid solution used, resulting in waste acid consisting primarily of sulfuric acid that may contain the remaining nitric acid depending on the circumstances.

Since the nitrated aromatic compound produced is dispersed in the waste acid, the nitrated aromatic compound and the waste acid undergo the liquid-liquid separation to separate the waste acid from the nitrated aromatic compound. The waste acid separated is circulated and reused for the nitration. In this separation process, the waste acid that cannot be separated from the nitrated aromatic compound comes to be a loss.

When the waste acid is recycled, water corresponding to the product water in nitration and to the introduced water is condensed within the system or outside the system and is removed therefrom, so that it has a concentration of the order of e.g. 60-95 weight % for the reuse. A loss is generated in this condensation as well.

In the case of the sulfuric acid, the total loss amounts to e.g. 0.01-1 weight %/h with respect to the total amount of sulfuric acid.

The polyamine producing reactor 23 is not limited to any particular one, as long as it is a reactor for performing reduction of a nitro group of the nitrated aromatic compound to an amino group. The polyamine producing reactor 23 is properly selected from a reactor equipped with a stirring vane, a fluid bed reactor, a fixed bed reactor, etc. Preferably, the polyamine producing reactor 23 is configured as a multistage tank. Further, the polyamine producing reactor 23 is connected to the polyisocyanate producing reactor 25 via the connection line 30.

Hydrogenerated catalyst (reduction catalyst) is charged in the polyamine producing reactor 23, to reduce the nitro group of the nitrated aromatic compound to the amino group, and the hydrogen gas ($H_2$) is continuously supplied to the polyamine producing reactor 23.

The hydrogenerated catalyst is not limited to any particular one. It can be selected from known catalysts containing metal, such as Ni, Mo, Fe, Co, Cu, Pt, Pd, and Rh. Industrially, palladium carbon catalyst or Raney nickel catalyst is preferably used. An amount of the hydrogenerated catalyst used is e.g. 0.001-1 parts by weight, or preferably 0.01-0.1 parts by weight, per 100 parts by weight of the nitrated aromatic compound supplied, though it is not particularly limited thereto.

The nitrated aromatic compound is continuously supplied from the nitration reactor 22 to the polyamine producing reactor 23 via the connection line 30. Then, the nitro group of the nitrated aromatic compound is reduced to the amino group (polyamine production process). In this polyamine production process, the polyamine producing reactor 23 is set at e.g. 0-10 MPa-gauge, or preferably 0.1-7 MPa-gauge, at e.g. 20-250° C., or preferably 50-200° C.

Thus, the nitro group of the nitrated aromatic compound is reduced to the amino group in the polyamine producing reactor 23. To be more specific, when the nitrated aromatic compound is dinitrotoluene, toluene diamine (TDA) is produced as the polyamine.

On the other hand, when the nitrated aromatic compound is nitrobenzene, aniline is produced. When the nitrated aromatic compound is nitrobenzene, in other words, when benzene is used as the aromatic raw material, the polyamine producing reactor 23 is provided with a condensation tank, arranged at a location downstream of the reactor, for condensing aniline and formaldehyde to produce polymethylene polyphenyl polyamine.

A known reactor is used as the condensation tank. The condensation tank is preferably configured as the multistage tank. The aniline produced, formaldehyde and the hydrochloric acid are continuously supplied to the condensation tank to produce polymethylene polyphenyl polyamine (MDA).

The formaldehyde is supplied continuously in the proportion of e.g. 0.3-0.6 mol, or preferably 0.4-0.5 mol, per mol of aniline.

The hydrochloric acid is supplied continuously in the proportion of e.g. 0.2-1 mol, or preferably 0.3-0.7 mol, per mol of aniline.

Then, the aniline is continuously supplied to the condensation tank. As a result of this, the aniline and the formaldehyde are condensed in the presence of hydrochloric acid to produce polymethylene polyphenyl polyamine (MDA) as the polyamine.

Pursuant to Japanese Unexamined Patent Publication No. 3-294249, the aniline and the formaldehyde can be condensed in the presence of hydrochloric acid to produce polymethylene polyphenyl polyamine (MDA) as the polyamine.

The carbonyl chloride producing reactor 24 is not limited to any particular one, as long as it is a reactor for allowing the chlorine ($Cl_2$) to react with monoxide (CO) to produce carbonyl chloride ($COCl_2$). For example, the carbonyl chloride producing reactor 24 comprises the fixed bed reactor packed with activated carbon catalyst, and the like. Further, the carbonyl chloride producing reactor 24 is connected to the polyisocyanate producing reactor 25 via the connection line 30.

Chlorine gas and carbon monoxide gas, serving as raw materials, are supplied to the carbonyl chloride producing reactor 24 in such a proportion that the carbon monoxide is supplied more than the chlorine by 1-10 mol %. When chlorine is oversupplied, there is a possibility that an aromatic ring and a hydrocarbon group of polyisocyanate may be chlorinated in the polyisocyanate producing reactor 25 by the oversupplied chlorine.

An amount of chlorine gas supplied and an amount of carbon monoxide gas supplied are properly determined on the basis of an amount of polyisocyanate produced and an amount of hydrogen chloride gas produced secondarily. The chlorine gas supplied from a dehydration column 29 via the chlorine supply line 32 is used as the chlorine gas, as mentioned later.

Then, in the carbonyl chloride producing reactor 24, the chlorine and the carbon monoxide react with each other to produce carbonyl chloride (carbonyl chloride production process). In this reaction, the carbonyl chloride producing reactor 24 is set at 0-500° C. and 0-5 MPa-gauge, for example.

The carbonyl chloride obtained may be put in a liquefied state by being properly cooled to be liquefied in the carbonyl chloride producing reactor 24 or may be put in a solution state by being absorbed in an adequate solvent. If necessary, the carbon monoxide contained in the carbonyl chloride obtained may be removed and then the resulting carbonyl chloride can be resupplied to the carbonyl chloride producing reactor 24.

When at least a part of carbonyl chloride is put in the liquefied state and/or solution state, a concentration of carbon monoxide contained in the carbonyl chloride can be reduced. This can improve a ratio of conversion of hydrogen chloride to chlorine in hydrogen chloride oxidation reaction mentioned later. The carbonyl chloride can be put in the liquefied state, for example, using a condenser provided at a location downstream of the fixed bed reactor to liquefy the carbonyl chloride in the carbonyl chloride producing reactor 24. In this liquefaction process, a concentration of carbon monoxide contained in the carbonyl chloride is preferably set at 1 weight % or less.

The polyisocyanate producing reactor 25 is not limited to any particular one, as long as it is a reactor for performing the reaction of carbonyl chloride with polyamine to produce polyisocyanate. The polyisocyanate producing reactor 25 includes, for example, a reactor equipped with a stirring vane and a reactor having a perforated plate. Preferably, the polyisocyanate producing reactor 25 is configured as a multistage tank. The polyisocyanate producing reactor 25 is connected to the hydrogen chloride purifying column 26 through the connection line 30.

The carbonyl chloride produced in the carbonyl chloride producing reactor 24 is supplied to the polyisocyanate producing reactor 25 from the carbonyl chloride producing reactor 24 via the connection line 7. In addition, the polyamine produced in the polyamine producing reactor 23 is also supplied to the polyisocyanate producing reactor 25 from the polyamine producing reactor 23 via the connection line 30.

The carbonyl chloride is supplied from the carbonyl chloride producing reactor 24 in a gaseous state as it is or in the above-mentioned liquefied or solution state in such a proportion that carbonyl chloride is supplied more than polyamine by 1-60 mol.

Though the polyamine may be supplied directly, it is preferable that the polyamine is previously dissolved in a solvent to produce a 5-30 weight % solution before being supplied.

The solvent used is not limited to any particular one. The solvents that may be used include, for example, aromatic hydrocarbons, such as toluene and xylene, halogenated hydrocarbons, such as chlorotoluene, chlorobenzene, and dichlorobenzene, esters, such as butyl acetate and amyl acetate, and ketones, such as methylisobutyl ketone and methyl ethyl ketone. Preferably, chlorobenzene and dichlorobenzene can be used.

In the polyisocyanate producing reactor 25, the carbonyl chloride and the polyamine react with each other to produce polyisocyanate, while also hydrochloric gas (HCl gas) is produced secondarily (polyisocyanate production process). In this reaction, the above-mentioned solvent is added in the polyisocyanate producing reactor 25 separately or together with the polyamine. The polyisocyanate producing reactor 25 is set at 0-250° C. and 0-5 MPa-gauge, for example.

The polyisocyanate produced undergoes aftertreatments, such as degasification, desolvating, and tar cut, and then purified, before it is provided as the raw material of polyurethane.

For example, when the polyamine is toluene diamine (TDA), tolylene diisocyanate (TDI) is provided as the polyisocyanate. When the polyamine is polymethylene polyphenyl polyamine (MDA), polymethylene polyphenyl polyisocyanate (MDI) is provided as the polyisocyanate.

The hydrochloric gas produced secondarily is supplied to the hydrogen chloride purifying column 26 via the connection line 30, together with the entrained solvent and carbonyl chloride.

The hydrogen chloride purifying column 26 is not limited to any particular one, as long as it can purify the hydrochloric gas by separating the entrained solvent and carbonyl chloride therefrom. For example, the hydrogen chloride purifying column 26 includes a tray column and a packed column, which are equipped with a condenser. The hydrogen chloride purifying column 26 is connected to the hydrogen chloride oxidizing reactor 28 via the connection line 30.

In the hydrogen chloride purifying column 26, the carbonyl chloride is condensed by the condenser or absorbed by the solvent, whereby the carbonyl chloride is separated from the hydrochloric gas. Further, a slight amount of solvent in the hydrogen chloride is separated from the hydrochloric gas by being absorbed in activated carbon and the like.

In the hydrogen chloride purifying column 26, a concentration of an organic material in the hydrochloric gas is preferably reduced to be 1 weight % or less, or preferably 0.1 weight % or less, and a concentration of carbon monoxide in the hydrochloric gas is preferably reduced to be 10 volume % or less, or preferably 3 volume % or less. By reducing impurities in the hydrochloric gas to such a level, disadvantageous effects on the catalyst, such as decreased activity or partial deactivation of the catalyst, can be reduced or prevented in the hydrogen chloride oxidation reaction mentioned later. This can realize improvement in basic unit, equalization in temperature distribution in hydrogen chloride oxidation reaction, and equalization in temperature distribution of the reactor and thus stabilization of the reactor. Further, this can improve a conversion ratio of hydrochloric gas to chlorine.

Then, the hydrochloric gas purified is supplied to the hydrogen chloride oxidizing reactor 28.

The hydrogen chloride oxidizing reactor 28 is not limited to any particular one, as long as it is a reactor for performing oxidation of the hydrochloric gas to produce chlorine ($Cl_2$). For example, the hydrogen chloride oxidizing reactor 28 includes a fluid bed reactor using chromium oxide as the catalyst and a fixed bed reactor using ruthenium oxide as the catalyst. The hydrogen chloride oxidizing reactor 28 is connected to the hydrogen chloride absorbing column 27 via the connection line 30.

When the hydrogen chloride oxidizing reactor 28 comprises the fluid bed reactor, at least 0.25 mol of oxygen per mol of hydrogen chloride contained in the hydrochloric gas is supplied for the reaction in the presence of chromium oxide at 0.1-5 MPa-gauge and 300-500° C., with reference to Japanese Unexamined Patent Publication No. 62-275001, for example. An amount of hydrochloric gas supplied is in the range of e.g. 0.2-1.8 $Nm^3$/h-kg-catalyst.

When the hydrogen chloride oxidizing reactor 28 comprises the fixed bed reactor, at least 0.25 mol of oxygen per mol of hydrogen chloride contained in the hydrochloric gas is supplied for the reaction in the presence of ruthenium-containing catalyst at 0.1-5 MPa and 200-500° C., with reference to Japanese Unexamined Patent Publication No. 2000-272906, for example.

Then, in the hydrogen chloride oxidizing reactor 28, the hydrochloric gas is oxidized by oxygen ($O_2$), so that chlorine is produced and water ($H_2O$) is produced secondarily (hydrogen chloride oxidation process). In this oxidation reaction (hydrogen chloride oxidation reaction), a conversion ratio of hydrogen chloride to chlorine is e.g. 60% or more, or preferably 70-95%.

The mixture of chlorine, water produced secondarily, and unoxidized (unreacted) hydrogen chloride gas (including hydrochloric acid water produced by water absorption) produced in the hydrogen chloride oxidizing reactor 28 is supplied to the hydrogen chloride absorbing column 27 via the connection line 30.

The hydrogen chloride absorbing column 27 is not limited to any particular one, as long as it can adjust a concentration of the hydrochloric acid water (aqueous solution of hydrogen chloride: HClaq) by making the unoxidized (unreacted) hydrogen chloride gas (including hydrochloric acid water produced by water absorption) absorbed in water or hydrochloric acid water. The hydrogen chloride absorbing column 27 includes a known absorbing column. The hydrogen chloride absorbing column 27 is connected to the dehydration column 29 via the connection line 30.

In the hydrogen chloride absorbing column 27, the hydrogen chloride gas contained in the mixture supplied thereto from the hydrogen chloride oxidizing reactor 28 via the connection line 30 is absorbed in water and hydrochloric acid water thereby to produce hydrochloric acid (hydrochloric acid production process). The hydrochloric acid thus produced is provided for industrial purpose as it is or after purified properly.

Since the hydrochloric acid produced in the hydrogen chloride absorbing column 27 is provided as it is in a desired concentration for industrial purpose, a concentration of the hydrochloric acid (a concentration of hydrogen chloride contained in the hydrochloric acid) is adjusted to a desired value by regulating an amount of water supplied to the hydrogen chloride absorbing column 27. Alternatively, the concentration of the hydrochloric acid may be adjusted in such a process in which after the hydrochloric acid once absorbed is heated to produce hydrochloric gas again, the hydrochloric gas thus reproduced is absorbed in a predetermined amount of water.

Then, in the hydrogen chloride absorbing column 27, the hydrochloric gas contained in the mixture supplied from the hydrogen chloride oxidizing reactor 28 via the connection line 30 is removed as hydrochloric acid by being absorbed in water, thereby to produce a mixed gas comprising primarily chlorine not absorbed in water. This mixed gas is the mixture of chlorine and water corresponding to vapor pressure. This mixed gas is supplied to the dehydration column 29 via the connection line 30.

The dehydration column 29 is not limited to any particular one, as long as it can allow the mixed gas of chlorine and water to contact with sulfuric acid ($H_2SO_4$) to remove water from the mixed gas. The dehydration column 29 includes a known dehydration column. The dehydration column 29 is connected to the nitration reactor 22 via the sulfuric acid supply line 31 and also connected to the carbonyl chloride producing reactor 24 via the chlorine supply line 32.

Figure 4:
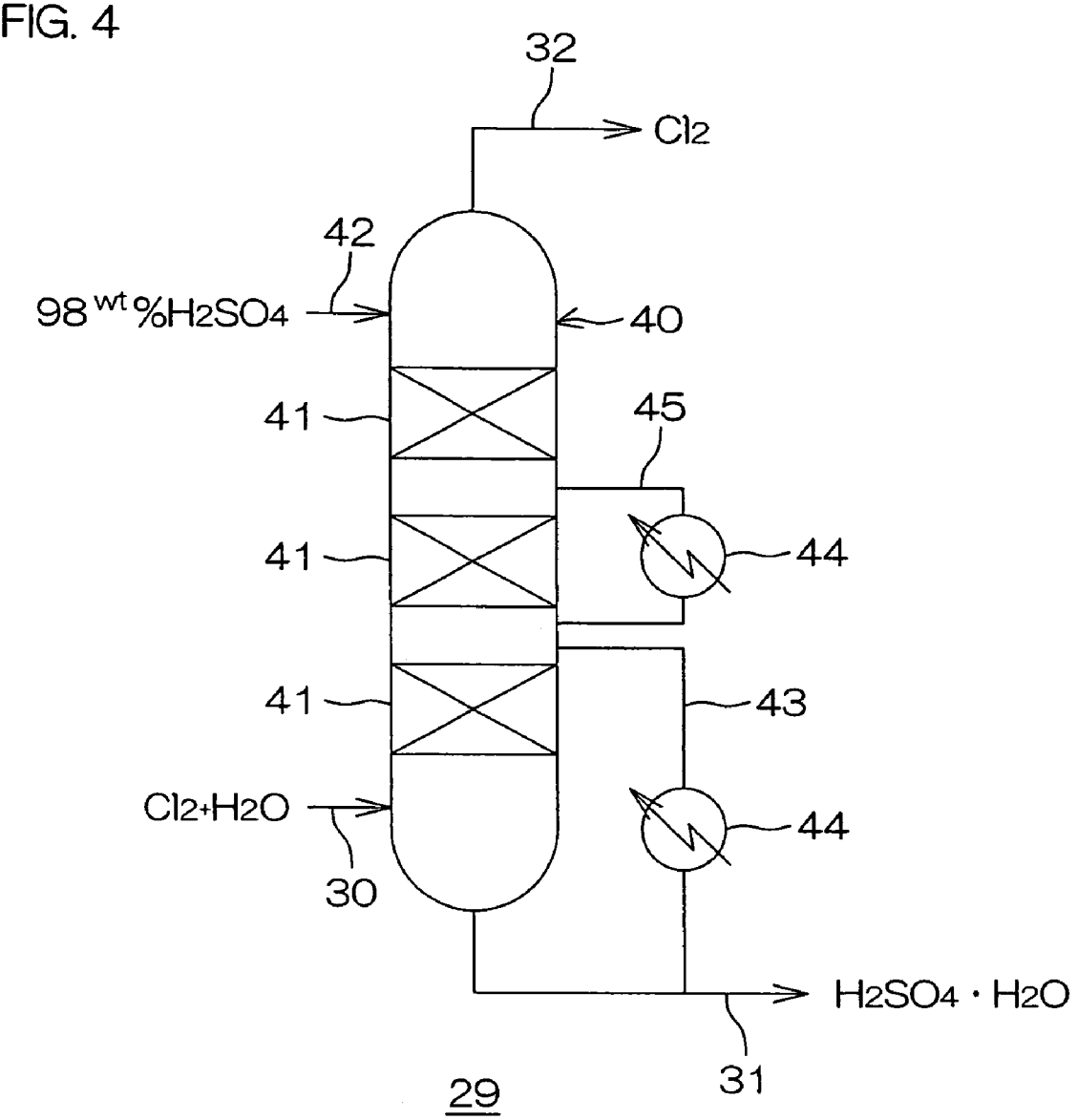
FIG. 4 is a schematic block diagram showing an embodiment of a dehydration column shown in FIG. 3.

For example, a dehydration column 40 shown in FIG. 4 is used as the dehydration column 29.

As shown in FIG. 4, the dehydration column 40 is in a sealed cylindrical form extending vertically and is provided with filling chambers 41 at upper, middle and lower portions thereof. These filling chambers 41 are spaced apart from each other and are packed with filler such as Raschig ring, Berl saddle, and the like.

The dehydration column 40 connects at its lower portion with the connection line 30 connected to the hydrogen chloride absorbing column 27 and connects at its upper portion with a sulfuric acid falling line 42 for allowing the falling of the sulfuric acid. Further, it connects at its bottom with the sulfuric acid supply line 31 and connects at its top with the chlorine supply line 32.

Further, the dehydration column 40 connects with a lower circulation line 43 for connecting its portion between the lower filling chamber 41 and the middle filling chamber 41 to the sulfuric acid supply line 31. A cooler 44 is interposed in the lower circulation line 43. The dehydration column 40 also connects with an upper circulating line 45 for connecting its portion between the lower filling chamber 41 and the middle filling chamber 41 to its portion between the middle filling chamber 41 and the upper filling chamber 41. A cooler 44 is interposed in the upper circulation line 45.

The mixed gas of chlorine and water is continuously supplied to the dehydration column 40 from the lower connection line 30, while also at least 97 weight % of sulfuric acid (aqueous solution), or preferably 98 weight % of sulfuric acid (aqueous solution) is continuously supplied thereto from the upper sulfuric acid falling line 42.

This allows falling of the sulfuric acid, thus allowing the sulfuric acid to contact with the mixed gas continuously in the countercurrent manner and allowing the effective gas-liquid contact in the respective filling chambers 41 in particular, to absorb the water contained in the mixed gas for dehydration (dehydration process). The hydrochloric gas obtained from the dehydration of the mixed gas is drained to the chlorine supply line 32 continuously.

On the other hand, the sulfuric acid absorbing water becomes e.g. 70-80 weight % (aqueous solution) sulfuric acid and thereafter is drained to the sulfuric acid supply line 31 continuously.

When the sulfuric acid absorbs water, heat is generated in the dehydration column 40. However, the aqueous sulfuric acid solution is partly circulated in the dehydration column 40 via the lower circulation line 43 and the upper circulation line 45, and the internal temperature of the dehydration column 40 is controlled to e.g. 0-60° C., or preferably 10-40° C., by the coolers 44 interposed in the lower circulation line 43 and the upper circulation line 45, respectively.

Then, the sulfuric acid drained from the dehydration column 29 to the sulfuric acid supply line 31 and absorbing water is supplied to the nitration reactor 22 via the sulfuric acid supply line 31 and is used as the sulfuric acid for the nitration. An amount of sulfuric acid supplied from the sulfuric acid supply line 31 to the nitration reactor 22 (an amount supplied per means of time) corresponds to an amount of sulfuric acid lost in the nitration reactor 22. The amount of sulfuric acid thus supplied is adjusted by adjusting an amount of sulfuric acid supplied from the sulfuric acid falling line 42 in the dehydration column 40.

The sulfuric acid drained from the dehydration column 29 to the sulfuric supply line 31 and absorbing water may be condensed so that it can have a concentration of the order of e.g. 88-95 weight % before it is supplied to the nitration reactor 22 via the sulfuric supply line 31. In this case, the sulfuric acid and water are entrained to generate a loss of sulfuric acid. In the adjustment process described above, the loss including the amount of loss resulting from the condensation of the sulfuric acid is also adjusted.

Further, the chlorine drained from the dehydration column 29 to the chlorine supply line 32 and dried by the dehydration is supplied to the carbonyl chloride producing reactor 24 via the chlorine supply line 32 and is used as the raw material for producing the carbonyl chloride.

In addition to the chlorine (the recycled chlorine) supplied from the chlorine supply line 32, chlorine (added chlorine) separately prepared as raw material is also supplied to the carbonyl chloride producing reactor 24. An amount of added chlorine supplied is set to correspond to a required amount of hydrogen chloride (or a shortage of the recycled chlorine) for producing the hydrochloric acid in the hydrogen chloride absorbing column 27. The added chlorine may be purchased from outside, if required. Alternatively, the polyisocyanate production system 21 may include added chlorine production equipment for producing chlorine by a process such as electrolyzation separate from the polyisocyanate production method so that the added chlorine may be supplied from such added chlorine production equipment.

When the added chlorine is supplied corresponding to the required amount of added chlorine for producing the hydrochloric acid in the hydrogen chloride absorbing column 27, a mass balance of the polyisocyanate production system 21 can be stabilized, while the hydrochloric acid of a desired concentration can be achieved from the hydrogen chloride absorbing column 27.

In this polyisocyanate production system 21, since the sulfuric acid used for the dehydration in the dehydration column 29 can be used for the nitration of the aromatic raw material in the nitration reactor 22, the effective usage of the sulfuric acid used for the dehydration can be achieved and reduction of the production cost of polyisocyanate can be achieved.

That is, in this polyisocyanate production system 21, when the mixed gas of chlorine and water is dehydrated in the dehydration column 29, using at least 97 weight % concentrated sulfuric acid, the dehydration efficiency can be improved remarkably.

On the other hand, the sulfuric acid, after dehydrated, absorbs water, so that its concentration reduces to 70-80 W/W %. When the sulfuric acid is tried to be condensed so that it can have a concentration of 97 W/W % or more for the circulation use, the number of processes required for the concentration is increased significantly, causing cost rise. On the other hand, when the sulfuric acid after dehydration is disposed without being recycled, the consumption of the sulfuric acid increases significantly, then still causing inevitable cost rise.

However, in this polyisocyanate production system 21, since the sulfuric acid used for the dehydration in the dehydration column 29 is reused for the nitration of the aromatic raw material in the nitration reactor 22, the sulfuric acid used for the dehydration can be utilized effectively without any need to be condensed to a high concentration, thus achieving reduced production cost of polyisocyanate.

Further, in this polyisocyanate production system 21, since the amount per means of time of sulfuric acid supplied from the sulfuric acid falling line 42 is adjusted in the dehydration column 29 to correspond to an amount of sulfuric acid lost in the nitration reactor 22, there is no need to add the sulfuric acid to the nitration reactor 22, thus allowing further effective use of the sulfuric acid.

Further, in this polyisocyanate production system 21, the chlorine dried in the dehydration column 29 by the dehydration is purified by a known method on an as-needed basis so that it is reused as the raw material for producing the carbonyl chloride in the carbonyl chloride producing reactor 24, the chlorine can be recycled without being drained to the outside of the system. Hence, the hydrochloric gas produced secondarily can be used effectively, while achieving reduction of environmental burdens.

INDUSTRIAL APPLICABILITY

The present invention is effectively applicable to a polyisocyanate production method for producing polyisocyanate used as a raw material of polyurethane and is also effectively applicable to a polyisocyanate production system for performing the polyisocyanate production method.

The invention claimed is:
1. A polyisocyanate production method comprising,
a carbonyl chloride production process of producing carbonyl chloride by allowing chlorine to react with carbon monoxide,
a polyisocyanate production process of producing polyisocyanate by allowing the carbonyl chloride produced in the carbonyl chloride production process to react with polyamine, a chlorine production process of producing chlorine by oxidizing hydrogen chloride produced secondarily in the polyisocyanate production process, and a hydrochloric acid production process of producing hydrochloric acid by allowing at least a part of the hydrogen chloride produced secondarily in the polyisocyanate production process and unoxidized hydrogen chloride in the chlorine production process to be absorbed or mixed in water, wherein the carbonyl chloride is produced by allowing the chlorine produced in the chlorine production process to react with carbon monoxide in the carbonyl chloride production process.

2. The polyisocyanate production method according to claim 1, wherein in the carbonyl chloride production process, chlorine is additionally supplied together with the chlorine produced in the chlorine production process so as to provide hydrogen chloride in the hydrochloric acid production process.

3. The polyisocyanate production method according to claim 1, wherein at least a part of the carbonyl chloride produced in the carbonyl chloride production process is put in a liquefied state and/or a solution state before the reaction with polyamine.

4. A polyisocyanate production method comprising, a polyamine production process of producing polymethylene polyphenylene polyamine by allowing aniline to react with formaldehyde, using an acid catalyst containing hydrochloric acid, a carbonyl chloride production process of producing carbonyl chloride by allowing chlorine to react with carbon monoxide, a polyisocyanate production process of producing polymethylene polyphenylene polyisocyanate by allowing the carbonyl chloride produced in the carbonyl chloride production process to react with polymethylene polyphenylene polyamine produced in the polyamine production process, a chlorine production process of producing chlorine by oxidizing hydrogen chloride produced secondarily in the polyisocyanate production process, and a hydrochloric acid production process of producing hydrochloric acid by allowing at least a part of hydrogen chloride produced secondarily in the polyisocyanate production process and unoxidized hydrogen chloride in the chlorine production process to be absorbed or mixed in water, wherein the chlorine produced in the chlorine production process is allowed to react with carbon monoxide in the carbonyl chloride production process to produce carbonyl chloride, and the hydrochloric acid produced in the hydrochloric acid production process is used as the acid catalyst in the polyamine production process.

5. A polyisocyanate production method comprising, a carbonyl chloride production process of producing carbonyl chloride by allowing chlorine to react with carbon monoxide, a polyisocyanate production process of producing tolylene diisocyanate by allowing the carbonyl chloride produced in the carbonyl chloride production process to react with tolylene diamine, a chlorine production process of producing chlorine by oxidizing hydrogen chloride produced secondarily in the polyisocyanate production process, and a hydrochloric acid production process of producing the hydrochloric acid by allowing at least a part of the hydrogen chloride produced secondarily in the polyisocyanate production process, and unoxidized hydrogen chloride in the chlorine production process, to be absorbed or mixed in water, wherein the chlorine produced in the chlorine production process is allowed to react with carbon monoxide in the carbonyl chloride production process to produce carbonyl chloride.

6. A polyisocyanate production method comprising, a carbonyl chloride production process of producing carbonyl chloride by allowing chlorine to react with carbon monoxide, a polyisocyanate production process of producing polyisocyanate by allowing the carbonyl chloride produced in the carbonyl chloride production process to react with polyamine, a chlorine production process of producing chlorine to be used in the carbonyl chloride production process by oxidizing hydrogen chloride produced secondarily in the polyisocyanate production process, and a hydrochloric acid production process of producing hydrochloric acid by allowing at least a part of the hydrogen chloride produced secondarily in the polyisocyanate production process and unoxidized hydrogen chloride in the chlorine production process to be absorbed or mixed in water, wherein a start-up operation is first performed by starting production of carbonyl chloride in the carbonyl chloride production process, starting production of polyisocyanate in the polyisocyanate production process, and starting production of chlorine in the chlorine production process, then a load-up operation, in which any one of processes, i.e., a process of increasing an amount of carbonyl chloride produced in the carbonyl chloride production process, a process of increasing an amount of polyisocyanate produced in the polyisocyanate production process, and a process of increasing an amount of chlorine produced in the chlorine production process, is selectively performed, and then the two other processes are performed, is repeatedly performed, until an amount of polyisocyanate produced reaches a predetermined amount.

7. The polyisocyanate production method according to claim 6, wherein in the start-up operation, after the production of the carbonyl chloride starts in the carbonyl chloride production process, the production of polyisocyanate starts in the polyisocyanate production process and then the production of chlorine starts in the chlorine production process.

8. The polyisocyanate production method according to claim 6, wherein in the load-up operation, after an amount of carbonyl chloride produced is increased in the carbonyl chloride production process, an amount of polyisocyanate produced is increased in the polyisocyanate production process and then an amount of chlorine produced is increased in the chlorine production process.

9. The polyisocyanate production method according to claim 6, wherein in the chlorine production process, hydrogen chloride is oxidized in a fluid bed reactor, and in the start-up operation, a warming-up operation of the fluid bed reactor is performed before the production of chlorine starts in the chlorine production process.

10. The polyisocyanate production method according to claim 6, wherein in the chlorine production process, hydrogen chloride is oxidized in a fixed bed reactor, and in the start-up operation, a warming-up operation of the fixed bed reactor is performed before the production of chlorine starts in the chlorine production process.

11. A polyisocyanate production method comprising,
a carbonyl chloride production process of producing carbonyl chloride by allowing chlorine to react with carbon monoxide,
a polyisocyanate production process of producing polyisocyanate by allowing the carbonyl chloride produced in the carbonyl chloride production process to react with polyamine,
a chlorine production process of producing chlorine to be used in the carbonyl chloride production process by oxidizing hydrogen chloride produced secondarily in the polyisocyanate production process, and
a hydrochloric acid production process of producing hydrochloric acid by allowing at least a part of the hydrogen chloride produced secondarily in the polyisocyanate production process and unoxidized hydrogen chloride in the chlorine production process to be absorbed or mixed in water,
wherein a start-up operation, in which after chlorine of raw material prepared previously and carbon monoxide are allowed to react with each other in the carbonyl chloride production process to produce carbonyl chloride, the carbonyl chloride produced is allowed to react with polyamine in the polyisocyanate production process to produce polyisocyanate and then the hydrogen chloride produced secondarily is oxidized in the chlorine production process to produce chlorine to be used in the carbonyl chloride production process, is first performed,
and then a load-up operation, in which after the chlorine of raw material and the chlorine produced in the chlorine production process are allowed to react with carbon monoxide in the carbonyl chloride production process to produce carbonyl chloride, the carbonyl chloride produced is allowed to react with polyamine in the polyisocyanate production process to produce polyisocyanate and then the hydrogen chloride produced secondarily is oxidized in the chlorine production process to produce chlorine to be used in the carbonyl chloride production process, is repeatedly performed until an amount of polyisocyanate produced reaches a predetermined amount.

12. The polyisocyanate production method according to claim 11, wherein a fixed amount of chlorine of raw material is used in the carbonyl chloride production process in the start-up operation as well as in the load-up operation.

13. A polyisocyanate production method comprising,
a polyamine production process of producing polymethylene polyphenylene polyamine by allowing aniline to react with formaldehyde, using an acid catalyst containing hydrochloric acid,
a carbonyl chloride production process of producing carbonyl chloride by allowing chlorine to react with carbon monoxide,
a polyisocyanate production process of producing polymethylene polyphenylene polyisocyanate by allowing the carbonyl chloride produced in the carbonyl chloride production process to react with the polymethylene polyphenylene polyamine produced in the polyamine production process,
a chlorine production process of producing chlorine to be used in the carbonyl chloride production process by oxidizing hydrogen chloride produced secondarily in the polyisocyanate production process, and
a hydrochloric acid production process of producing hydrochloric acid to be used as the acid catalyst in the polyamine production process by allowing at least a part of the hydrogen chloride produced secondarily in the polyisocyanate production process and unoxidized hydrogen chloride in the chlorine production process to be absorbed or mixed in water,
wherein a start-up operation is first performed by starting production of polymethylene polyphenylene polyamine in the polyamine production process, starting production of carbonyl chloride in the carbonyl chloride production process, starting production of polymethylene polyphenylene polyisocyanate in the polyisocyanate production process, starting production of chlorine in the chlorine production process, and starting production of hydrochloric acid in the hydrochloric acid production process, and
then a load-up operation, in which any one of five processes, i.e., a process of increasing an amount of polymethylene polyphenylene polyamine produced in the polyamine production process, a process of increasing an amount of carbonyl chloride produced in the carbonyl chloride production process, a process of increasing an amount of polyisocyanate produced in the polyisocyanate production process, a process of increasing an amount of chlorine produced in the chlorine production process, and a process of increasing an amount of hydrochloric acid produced in the hydrochloric acid production process, is selectively performed, and then the four other processes are performed, is repeatedly performed until an amount of polymethylene polyphenylene polyisocyanate produced reaches a predetermined amount.

* * * * *